US012336686B2

(12) United States Patent
Levy et al.

(10) Patent No.: US 12,336,686 B2
(45) Date of Patent: Jun. 24, 2025

(54) MULTI-VIEWING ELEMENT ENDOSCOPE

(71) Applicant: EndoChoice, Inc., Alpharetta, GA (US)

(72) Inventors: Avi Levy, Herzliya (IL); Yaniv Kirma, Karcur (IL); Moshe Levi, Ganey Tikva (IL)

(73) Assignee: EndoChoice, Inc., Alpharetta, GA (US)

( * ) Notice: Subject to any disclaimer, the term of this patent is extended or adjusted under 35 U.S.C. 154(b) by 0 days.

(21) Appl. No.: 18/638,092

(22) Filed: Apr. 17, 2024

(65) Prior Publication Data

US 2024/0260818 A1 Aug. 8, 2024

Related U.S. Application Data

(63) Continuation of application No. 17/669,757, filed on Feb. 11, 2022, now Pat. No. 11,986,155, which is a
(Continued)

(51) Int. Cl.
*A61B 1/00* (2006.01)
*A61B 1/015* (2006.01)
(Continued)

(52) U.S. Cl.
CPC ........ *A61B 1/00181* (2013.01); *A61B 1/0008* (2013.01); *A61B 1/00091* (2013.01);
(Continued)

(58) Field of Classification Search
CPC .............. A61B 1/0008; A61B 1/00091; A61B 1/00096; A61B 1/00177; A61B 1/00179;
(Continued)

(56) References Cited

U.S. PATENT DOCUMENTS 3,639,714 A 2/1972 Fujimoto
3,955,064 A 5/1976 Demetrio
(Continued)

FOREIGN PATENT DOCUMENTS

CN 1376443 10/2002
CN 2829646 Y 10/2006
(Continued)

OTHER PUBLICATIONS

Brochure for US Endoscopy's AquaShield Water Bottle System, 2010.
(Continued)

*Primary Examiner* — Aaron B Fairchild
(74) *Attorney, Agent, or Firm* — Bookoff McAndrews PLLC

(57) ABSTRACT

There is provided herein a tip section of a multi-viewing element endoscope, the tip section comprising: two or more side-pointing viewing elements positioned at or in proximity to a distal end of said tip section, wherein each of said two or more side-pointing viewing elements having a discrete illuminator associated therewith, wherein the field of view provided by the two or more side-pointing viewing elements covers a front and side views; a working channel configured for insertion of a surgical tool; and a pathway fluid injector for inflating and/or cleaning a body cavity into which the endoscope is inserted.

10 Claims, 7 Drawing Sheets

Related U.S. Application Data continuation of application No. 16/567,333, filed on Sep. 11, 2019, now Pat. No. 11,278,190, which is a continuation of application No. 15/275,417, filed on Sep. 25, 2016, now Pat. No. 10,799,095, which is a continuation of application No. 13/212,627, filed on Aug. 18, 2011, now Pat. No. 9,492,063, which is a continuation-in-part of application No. 13/119,032, filed as application No. PCT/IL2010/000476 on Jun. 16, 2010, now Pat. No. 9,554,692.

(60) Provisional application No. 61/218,085, filed on Jun. 18, 2009.

(51) Int. Cl.
*A61B 1/018* (2006.01)
*A61B 1/04* (2006.01)
*A61B 1/05* (2006.01)
*A61B 1/06* (2006.01)
*A61B 1/07* (2006.01)
*A61B 1/12* (2006.01)
*A61B 1/31* (2006.01)
*A61B 10/06* (2006.01)

(52) U.S. Cl.
CPC .......... *A61B 1/00096* (2013.01); *A61B 1/015* (2013.01); *A61B 1/018* (2013.01); *A61B 1/04* (2013.01); *A61B 1/042* (2013.01); *A61B 1/05* (2013.01); *A61B 1/0615* (2013.01); *A61B 1/0676* (2013.01); *A61B 1/0684* (2013.01); *A61B 1/07* (2013.01); *A61B 1/126* (2013.01); *A61B 1/00009* (2013.01); *A61B 1/31* (2013.01); *A61B 10/06* (2013.01)

(58) Field of Classification Search
CPC ....... A61B 1/00181; A61B 1/015; A61B 1/05; A61B 1/0615; A61B 1/0676; A61B 1/0684; A61B 1/00193
See application file for complete search history.

(56) References Cited

U.S. PATENT DOCUMENTS

| | | |
|---|---|---|
| 4,037,588 A | 7/1977 | Heckele |
| 4,084,401 A | 4/1978 | Belardi |
| 4,253,448 A | 3/1981 | Terada |
| 4,261,345 A | 4/1981 | Yamaguchi |
| 4,402,313 A | 9/1983 | Yabe |
| 4,414,608 A | 11/1983 | Furihata |
| 4,439,030 A | 3/1984 | Ueda |
| 4,469,090 A | 9/1984 | Konomura |
| 4,494,549 A | 1/1985 | Namba |
| 4,522,196 A | 6/1985 | Cunningham |
| 4,565,423 A | 1/1986 | Ueda |
| 4,576,144 A | 3/1986 | Ishii |
| 4,588,294 A | 5/1986 | Siegmund |
| 4,590,923 A | 5/1986 | Watanabe |
| 4,641,635 A | 2/1987 | Yabe |
| 4,699,463 A | 10/1987 | D'Amelio |
| 4,708,126 A | 11/1987 | Toda |
| 4,727,859 A | 3/1988 | Lia |
| 4,736,732 A | 4/1988 | Shimonaka |
| 4,753,222 A | 6/1988 | Morishita |
| 4,764,001 A | 8/1988 | Yokota |
| 4,794,913 A | 1/1989 | Shimonaka |
| 4,801,792 A | 1/1989 | Yamasita |
| 4,841,952 A | 6/1989 | Sato |
| 4,846,154 A | 7/1989 | MacAnally |
| 4,868,644 A | 9/1989 | Yabe |
| 4,877,314 A | 10/1989 | Kanamori |
| 4,878,485 A | 11/1989 | Adair |
| 4,888,639 A | 12/1989 | Yabe |
| 4,902,115 A | 2/1990 | Takahashi |
| 4,905,670 A | 3/1990 | Adair |
| 4,914,521 A | 4/1990 | Adair |
| 4,974,075 A | 11/1990 | Nakajima |
| 4,976,522 A | 12/1990 | Igarashi |
| 4,982,724 A | 1/1991 | Saito |
| 4,984,878 A | 1/1991 | Miyano |
| 4,998,182 A | 3/1991 | Krauter |
| 5,166,787 A | 11/1992 | Irion |
| 5,193,525 A | 3/1993 | Silverstein |
| 5,239,983 A | 8/1993 | Katsurada |
| 5,296,971 A | 3/1994 | Mori |
| 5,299,561 A | 4/1994 | Yoshimoto |
| 5,305,121 A | 4/1994 | Moll |
| 5,309,227 A | 5/1994 | Inoue |
| 5,313,934 A | 5/1994 | Wiita |
| 5,339,800 A | 8/1994 | Wiita |
| 5,359,456 A | 10/1994 | Kikuchi |
| 5,380,049 A | 1/1995 | Smowton |
| 5,398,056 A | 3/1995 | Yabe |
| 5,408,263 A | 4/1995 | Dolidon |
| 5,412,478 A | 5/1995 | Ishihara |
| 5,420,644 A | 5/1995 | Watanabe |
| 5,432,543 A | 7/1995 | Hasegawa |
| 5,436,767 A | 7/1995 | Suzuki |
| 5,447,148 A | 9/1995 | Oneda |
| 5,452,391 A | 9/1995 | Chou |
| 5,460,167 A | 10/1995 | Yabe |
| 5,475,420 A | 12/1995 | Buchin |
| 5,483,951 A | 1/1996 | Frassica |
| 5,485,316 A | 1/1996 | Mori |
| 5,489,256 A | 2/1996 | Adair |
| 5,507,717 A | 4/1996 | Kura |
| 5,512,940 A | 4/1996 | Takasugi |
| 5,515,449 A | 5/1996 | Tsuruoka |
| 5,518,501 A | 5/1996 | Oneda |
| 5,518,502 A | 5/1996 | Kaplan |
| 5,547,455 A | 8/1996 | McKenna |
| 5,547,457 A | 8/1996 | Tsuyuki |
| 5,550,582 A | 8/1996 | Takasugi |
| 5,585,840 A | 12/1996 | Watanabe |
| 5,587,839 A | 12/1996 | Miyano |
| 5,589,874 A | 12/1996 | Buchin |
| 5,592,216 A | 1/1997 | Uehara |
| 5,605,530 A | 2/1997 | Fischell |
| 5,609,560 A | 3/1997 | Ichikawa |
| 5,617,136 A | 4/1997 | Iso |
| 5,630,782 A | 5/1997 | Adair |
| 5,653,677 A | 8/1997 | Okada |
| 5,656,011 A | 8/1997 | Uihlein |
| 5,662,588 A | 9/1997 | Iida |
| 5,675,378 A | 10/1997 | Takasugi |
| 5,679,110 A | 10/1997 | Hamazaki |
| 5,685,823 A | 11/1997 | Ito |
| 5,701,155 A | 12/1997 | Wood |
| 5,702,345 A | 12/1997 | Wood |
| 5,702,347 A | 12/1997 | Yabe |
| 5,707,344 A | 1/1998 | Nakazawa |
| 5,716,323 A | 2/1998 | Lee |
| 5,725,474 A | 3/1998 | Yasui |
| 5,725,476 A | 3/1998 | Yasui |
| 5,725,477 A | 3/1998 | Yasui |
| 5,728,045 A | 3/1998 | Komi |
| 5,751,340 A | 5/1998 | Strobl |
| 5,764,809 A | 6/1998 | Nomami |
| 5,777,797 A | 7/1998 | Miyano |
| 5,782,751 A | 7/1998 | Matsuno |
| 5,793,539 A | 8/1998 | Konno |
| 5,800,341 A | 9/1998 | McKenna |
| 5,812,187 A | 9/1998 | Watanabe |
| 5,830,124 A | 11/1998 | Suzuki |
| 5,836,894 A | 11/1998 | Sarvazyan |
| 5,852,511 A | 12/1998 | Tateyama |
| 5,860,913 A | 1/1999 | Yamaya |
| 5,870,234 A | 2/1999 | Ebbesmeier |
| 5,871,439 A | 2/1999 | Takahashi |
| 5,871,440 A | 2/1999 | Okada |
| 5,876,326 A | 3/1999 | Takamura |
| 5,879,284 A | 3/1999 | Tsujita |

(56) References Cited

U.S. PATENT DOCUMENTS

| | | | |
|---|---|---|---|
| 5,894,322 A | 4/1999 | Hamano |
| 5,912,764 A | 6/1999 | Togino |
| 5,913,817 A | 6/1999 | Lee |
| 5,914,810 A | 6/1999 | Watts |
| 5,916,148 A | 6/1999 | Tsuyuki |
| 5,929,901 A | 7/1999 | Adair |
| 5,930,424 A | 7/1999 | Heimberger |
| 5,933,275 A | 8/1999 | Igarashi |
| 5,933,282 A | 8/1999 | Tomioka |
| 5,936,773 A | 8/1999 | Togino |
| 5,940,126 A | 8/1999 | Kimura |
| 5,961,445 A | 10/1999 | Chikama |
| 5,969,888 A | 10/1999 | Sukekawa |
| 5,986,693 A | 11/1999 | Adair |
| 5,989,185 A | 11/1999 | Miyazaki |
| 5,993,037 A | 11/1999 | Tomioka |
| 5,995,136 A | 11/1999 | Hattori |
| 6,009,189 A | 12/1999 | Schaack |
| 6,025,873 A | 2/2000 | Nishioka |
| 6,043,839 A | 3/2000 | Adair |
| 6,069,698 A | 5/2000 | Ozawa |
| 6,080,104 A | 6/2000 | Ozawa |
| 6,104,540 A | 8/2000 | Hayakawa |
| 6,110,127 A | 8/2000 | Suzuki |
| 6,117,068 A | 9/2000 | Gourley |
| 6,124,989 A | 9/2000 | Oode |
| 6,139,175 A | 10/2000 | Tomioka |
| 6,139,490 A | 10/2000 | Breidenthal |
| 6,147,808 A | 11/2000 | Togino |
| 6,163,401 A | 12/2000 | Igarashi |
| 6,166,858 A | 12/2000 | Togino |
| 6,181,481 B1 | 1/2001 | Yamamoto |
| 6,184,923 B1 | 2/2001 | Miyazaki |
| 6,185,046 B1 | 2/2001 | Togino |
| 6,196,967 B1 | 3/2001 | Lim |
| 6,201,646 B1 | 3/2001 | Togino |
| 6,201,648 B1 | 3/2001 | Togino |
| 6,210,322 B1 | 4/2001 | Byrne |
| 6,211,904 B1 | 4/2001 | Adair |
| 6,215,517 B1 | 4/2001 | Takahashi |
| 6,217,500 B1 | 4/2001 | Helseth |
| 6,245,086 B1 | 6/2001 | Storz |
| 6,249,391 B1 | 6/2001 | Hayakawa |
| 6,260,994 B1 | 7/2001 | Matsumoto |
| 6,261,226 B1 | 7/2001 | McKenna |
| 6,275,255 B1 | 8/2001 | Adair |
| 6,295,368 B1 | 9/2001 | Hasegawa |
| 6,306,082 B1 | 10/2001 | Takahashi |
| 6,310,642 B1 | 10/2001 | Adair |
| 6,310,736 B1 | 10/2001 | Togino |
| 6,315,712 B1 | 11/2001 | Rovegno |
| 6,322,496 B1 | 11/2001 | Iida |
| 6,327,094 B1 | 12/2001 | Aoki |
| 6,327,101 B1 | 12/2001 | Miyano |
| 6,334,845 B1 | 1/2002 | Higuchi |
| 6,353,504 B1 | 3/2002 | Yamamoto |
| 6,375,610 B2 | 4/2002 | Verschuur |
| 6,387,045 B1 | 5/2002 | Takahashi |
| 6,398,723 B1 | 6/2002 | Kehr |
| 6,400,514 B2 | 6/2002 | Minami |
| 6,422,995 B2 | 7/2002 | Akiba |
| 6,425,857 B1 | 7/2002 | Rudischhauser |
| 6,450,950 B2 | 9/2002 | Irion |
| 6,461,304 B1 | 10/2002 | Tanaka |
| 6,464,631 B1 | 10/2002 | Girke |
| 6,464,633 B1 | 10/2002 | Hosoda |
| 6,468,201 B1 | 10/2002 | Burdick |
| 6,468,202 B1 | 10/2002 | Irion |
| 6,471,636 B1 | 10/2002 | Sano |
| 6,471,637 B1 | 10/2002 | Green |
| 6,473,116 B1 | 10/2002 | Takahashi |
| 6,476,851 B1 | 11/2002 | Nakamura |
| 6,500,115 B2 | 12/2002 | Krattiger |
| 6,514,210 B2 | 2/2003 | Ohara |
| 6,520,908 B1 | 2/2003 | Ikeda |
| 6,527,704 B1 | 3/2003 | Chang |
| 6,530,881 B1 | 3/2003 | Ailinger |
| 6,533,722 B2 | 3/2003 | Nakashima |
| 6,545,703 B1 | 4/2003 | Takahashi |
| 6,551,239 B2 | 4/2003 | Renner |
| 6,554,767 B2 | 4/2003 | Tanaka |
| 6,567,114 B2 | 5/2003 | Takahashi |
| 6,569,084 B1 | 5/2003 | Mizuno |
| 6,582,361 B2 | 6/2003 | Hirano |
| 6,589,168 B2 | 7/2003 | Thompson |
| 6,606,113 B2 | 8/2003 | Nakamura |
| 6,618,205 B2 | 9/2003 | Murayama |
| D481,125 S | 10/2003 | Hayamizu |
| 6,638,212 B1 | 10/2003 | Oshima |
| 6,638,214 B2 | 10/2003 | Akiba |
| 6,641,531 B2 | 11/2003 | Kehr |
| 6,656,111 B2 | 12/2003 | Fujii |
| 6,671,099 B2 | 12/2003 | Nagata |
| 6,677,983 B1 | 1/2004 | Takahashi |
| 6,677,984 B2 | 1/2004 | Kobayashi |
| 6,677,992 B1 | 1/2004 | Matsumoto |
| 6,692,430 B2 | 2/2004 | Adler |
| 6,692,431 B2 | 2/2004 | Kazakevich |
| 6,699,181 B2 | 3/2004 | Wako |
| 6,699,185 B2 | 3/2004 | Gminder |
| 6,704,052 B1 | 3/2004 | Togino |
| 6,712,760 B2 | 3/2004 | Sano |
| D490,898 S | 6/2004 | Hayamizu |
| 6,764,439 B2 | 7/2004 | Schaaf |
| 6,778,208 B2 | 8/2004 | Takeshige |
| 6,788,343 B1 | 9/2004 | Togino |
| 6,793,621 B2 | 9/2004 | Butler |
| 6,801,325 B2 | 10/2004 | Farr |
| 6,809,499 B2 | 10/2004 | Solingen |
| 6,809,866 B2 | 10/2004 | Xie |
| 6,829,003 B2 | 12/2004 | Takami |
| 6,832,984 B2 | 12/2004 | Stelzer |
| 6,844,985 B2 | 1/2005 | Murayama |
| 6,846,311 B2 | 1/2005 | Gatto |
| 6,849,043 B2 | 2/2005 | Kondo |
| 6,860,516 B2 | 3/2005 | Ouchi |
| 6,876,380 B2 | 4/2005 | Abe |
| 6,887,194 B2 | 5/2005 | Hart |
| 6,888,119 B2 | 5/2005 | Iizuka |
| 6,898,086 B2 | 5/2005 | Takami |
| 6,899,673 B2 | 5/2005 | Ogura |
| 6,900,829 B1 | 5/2005 | Ozawa |
| 6,900,950 B2 | 5/2005 | Nagata |
| 6,902,529 B2 | 6/2005 | Onishi |
| 6,903,761 B1 | 6/2005 | Abe |
| 6,918,693 B2 | 7/2005 | Ota |
| 6,921,362 B2 | 7/2005 | Ouchi |
| 6,930,705 B2 | 8/2005 | Tanaka |
| 6,933,962 B2 | 8/2005 | Yamamoto |
| 6,937,267 B1 | 8/2005 | Takahashi |
| 6,937,269 B2 | 8/2005 | Sugimoto |
| 6,943,821 B2 | 9/2005 | Abe |
| 6,943,822 B2 | 9/2005 | Iida |
| 6,944,031 B2 | 9/2005 | Takami |
| 6,945,929 B2 | 9/2005 | Ando |
| 6,947,070 B2 | 9/2005 | Takami |
| 6,950,691 B2 | 9/2005 | Uchikubo |
| 6,956,703 B2 | 10/2005 | Saito |
| 6,967,673 B2 | 11/2005 | Ozawa |
| 6,977,670 B2 | 12/2005 | Takahashi |
| 6,980,227 B2 | 12/2005 | Iida |
| 6,982,740 B2 | 1/2006 | Adair |
| 6,985,170 B1 | 1/2006 | Tsuyuki |
| 6,992,694 B2 | 1/2006 | Abe |
| 6,995,786 B2 | 2/2006 | Abe |
| 6,997,871 B2 | 2/2006 | Sonnenschein |
| 7,027,231 B2 | 4/2006 | Miyano |
| 7,030,904 B2 | 4/2006 | Adair |
| 7,037,258 B2 | 5/2006 | Chatenever |
| 7,042,488 B2 | 5/2006 | Higuchi |
| 7,043,153 B2 | 5/2006 | Takeyama |
| 7,046,270 B2 | 5/2006 | Murata |
| 7,050,086 B2 | 5/2006 | Ozawa |
| 7,074,181 B2 | 7/2006 | Futatsugi |

(56) References Cited

U.S. PATENT DOCUMENTS

| | | |
|---|---|---|
| 7,074,182 B2 | 7/2006 | Rovegno |
| 7,085,064 B2 | 8/2006 | Uzawa |
| 7,097,615 B2 | 8/2006 | Banik |
| 7,104,951 B2 | 9/2006 | Hasegawa |
| 7,108,656 B2 | 9/2006 | Fujikawa |
| 7,108,657 B2 | 9/2006 | Irion |
| 7,119,830 B2 | 10/2006 | Saito |
| 7,123,288 B2 | 10/2006 | Abe |
| 7,128,709 B2 | 10/2006 | Saruya |
| 7,129,472 B1 | 10/2006 | Okawa |
| 7,133,063 B2 | 11/2006 | Abe |
| D534,656 S | 1/2007 | Pilvisto |
| 7,156,863 B2 | 1/2007 | Sonnenschein |
| 7,158,314 B2 | 1/2007 | Fujii |
| 7,179,221 B2 | 2/2007 | Tsujita |
| 7,180,686 B2 | 2/2007 | Kato |
| 7,218,454 B2 | 5/2007 | Miyano |
| 7,223,231 B2 | 5/2007 | Akiba |
| 7,231,135 B2 | 6/2007 | Esenyan |
| 7,232,409 B2 | 6/2007 | Hale |
| 7,233,820 B2 | 6/2007 | Gilboa |
| 7,242,833 B2 | 7/2007 | Yang |
| 7,248,281 B2 | 7/2007 | Abe |
| 7,248,296 B2 | 7/2007 | Iketani |
| 7,252,633 B2 | 8/2007 | Obata |
| 7,255,676 B2 | 8/2007 | Higuchi |
| 7,262,797 B2 | 8/2007 | Weldum |
| 7,267,647 B2 | 9/2007 | Okada |
| 7,273,452 B2 | 9/2007 | Barbato |
| 7,277,120 B2 | 10/2007 | Gere |
| 7,280,140 B2 | 10/2007 | Henderson |
| 7,280,283 B1 | 10/2007 | Kasai |
| 7,282,025 B2 | 10/2007 | Abe |
| 7,306,588 B2 | 12/2007 | Loeb |
| 7,330,749 B1 | 2/2008 | Bhunachet |
| D564,659 S | 3/2008 | Hayashi |
| D564,660 S | 3/2008 | Hayashi |
| 7,351,202 B2 | 4/2008 | Long |
| 7,355,625 B1 | 4/2008 | Mochida |
| 7,358,987 B2 | 4/2008 | Takeshige |
| 7,365,768 B1 | 4/2008 | Ono |
| 7,371,211 B2 | 5/2008 | Akiba |
| 7,379,252 B2 | 5/2008 | Murayama |
| 7,384,308 B2 | 6/2008 | Boehnlein |
| 7,399,304 B2 | 7/2008 | Gambale |
| 7,400,341 B2 | 7/2008 | Abe |
| 7,401,984 B2 | 7/2008 | Pattie |
| 7,409,130 B2 | 8/2008 | Hatori |
| 7,420,586 B2 | 9/2008 | Higuchi |
| 7,427,263 B2 | 9/2008 | Hoeg |
| 7,431,619 B2 | 10/2008 | Boehnlein |
| 7,435,217 B2 | 10/2008 | Wiklof |
| 7,435,218 B2 | 10/2008 | Krattiger |
| 7,440,005 B2 | 10/2008 | Enomoto |
| 7,443,488 B2 | 10/2008 | Ogawa |
| 7,450,151 B2 | 11/2008 | Kaneko |
| 7,466,490 B2 | 12/2008 | Igarashi |
| 7,471,310 B2 | 12/2008 | Amling |
| 7,484,709 B2 | 2/2009 | Efinger |
| 7,486,449 B2 | 2/2009 | Miyano |
| 7,492,388 B2 | 2/2009 | Odlivak |
| 7,514,667 B2 | 4/2009 | Matsumoto |
| 7,518,632 B2 | 4/2009 | Konomura |
| 7,530,948 B2 | 5/2009 | Seibel |
| 7,542,069 B2 | 6/2009 | Tashiro |
| 7,553,276 B2 | 6/2009 | Iddan |
| 7,559,889 B2 | 7/2009 | Takahashi |
| 7,559,892 B2 | 7/2009 | Adler |
| 7,561,351 B2 | 7/2009 | Konno |
| 7,569,012 B2 | 8/2009 | Tanaka |
| 7,573,499 B2 | 8/2009 | Doguchi |
| 7,576,310 B2 | 8/2009 | Konno |
| 7,581,988 B2 | 9/2009 | Boehnlein |
| 7,582,055 B2 | 9/2009 | Komiya |
| 7,582,056 B2 | 9/2009 | Noguchi |
| 7,584,534 B2 | 9/2009 | Pease |
| 7,585,274 B2 | 9/2009 | Homma |
| 7,588,535 B2 | 9/2009 | Adler |
| 7,593,051 B2 | 9/2009 | Suda |
| 7,621,868 B2 | 11/2009 | Breidenthal |
| 7,621,869 B2 | 11/2009 | Ratnakar |
| 7,623,150 B2 | 11/2009 | Kobayashi |
| 7,627,189 B2 | 12/2009 | Donomae |
| 7,630,148 B1 | 12/2009 | Yang |
| 7,671,888 B2 | 3/2010 | Nogami |
| 7,683,927 B2 | 3/2010 | Higuchi |
| 7,695,429 B2 | 4/2010 | Hino |
| 7,699,772 B2 | 4/2010 | Pauker |
| 7,701,650 B2 | 4/2010 | Lin |
| 7,725,013 B2 | 5/2010 | Sugimoto |
| 7,728,867 B2 | 6/2010 | Fukuyama |
| 7,734,160 B2 | 6/2010 | Sudo |
| 7,746,566 B2 | 6/2010 | Mizusawa |
| 7,746,572 B2 | 6/2010 | Asami |
| 7,749,156 B2 | 7/2010 | Ouchi |
| 7,749,159 B2 | 7/2010 | Crowley |
| 7,758,495 B2 | 7/2010 | Pease |
| 7,758,499 B2 | 7/2010 | Adler |
| 7,772,786 B2 | 8/2010 | Hosoda |
| 7,773,110 B2 | 8/2010 | Abe |
| 7,773,122 B2 | 8/2010 | Irion |
| 7,773,318 B2 | 8/2010 | Takato |
| 7,775,971 B2 | 8/2010 | Fujimori |
| 7,775,973 B2 | 8/2010 | Okada |
| 7,789,822 B2 | 9/2010 | Suzuki |
| 7,800,656 B2 | 9/2010 | Takeuchi |
| RE41,807 E | 10/2010 | Yokoi |
| 7,821,529 B2 | 10/2010 | Mochida |
| 7,837,614 B2 | 11/2010 | Segawa |
| 7,841,880 B2 | 11/2010 | Ikeda |
| 7,846,090 B2 | 12/2010 | Pilvisto |
| 7,852,513 B2 | 12/2010 | Donomae |
| 7,893,956 B2 | 2/2011 | Ayrenschmalz |
| 7,896,802 B2 | 3/2011 | Otawara |
| 7,901,352 B2 | 3/2011 | Minami |
| 7,907,168 B2 | 3/2011 | Eino |
| 7,907,170 B2 | 3/2011 | Watanabe |
| 7,907,352 B2 | 3/2011 | Miyano |
| 7,914,443 B2 | 3/2011 | Uchimura |
| 7,918,788 B2 | 4/2011 | Lin |
| 7,938,773 B2 | 5/2011 | Kawai |
| 7,940,296 B2 | 5/2011 | Ogino |
| 7,942,814 B2 | 5/2011 | Remijan |
| 7,951,068 B2 | 5/2011 | Kura |
| 7,967,745 B2 | 6/2011 | Gilad |
| 7,976,462 B2 | 7/2011 | Wright |
| 7,995,093 B2 | 8/2011 | Takeuchi |
| 7,998,064 B2 | 8/2011 | Otawara |
| 8,002,696 B2 | 8/2011 | Suzuki |
| 8,027,101 B2 | 9/2011 | Suda |
| 8,033,992 B2 | 10/2011 | Hino |
| 8,035,684 B2 | 10/2011 | Wakito |
| 8,038,600 B2 | 10/2011 | Uchiyama |
| 8,043,207 B2 | 10/2011 | Adams |
| 8,060,172 B2 | 11/2011 | Ishihara |
| 8,063,962 B2 | 11/2011 | Hagihara |
| 8,066,631 B2 | 11/2011 | Wimmer |
| 8,072,483 B2 | 12/2011 | Tomioka |
| 8,072,537 B2 | 12/2011 | Schwarz |
| 8,072,693 B2 | 12/2011 | Togino |
| 8,075,477 B2 | 12/2011 | Nakamura |
| 8,075,478 B2 | 12/2011 | Campos |
| 8,098,441 B2 | 1/2012 | Sasamoto |
| 8,100,920 B2 | 1/2012 | Gambale |
| 8,102,415 B2 | 1/2012 | Iriyama |
| 8,105,233 B2 | 1/2012 | AbouElKheir |
| 8,113,846 B2 | 2/2012 | Wallaker |
| 8,125,514 B2 | 2/2012 | Sekiguchi |
| 8,125,515 B2 | 2/2012 | Hibi |
| 8,130,454 B2 | 3/2012 | Noguchi |
| 8,135,192 B2 | 3/2012 | Matsuzaki |
| 8,135,454 B2 | 3/2012 | Daniels |
| 8,139,296 B2 | 3/2012 | Ito |
| 8,144,191 B2 | 3/2012 | Kawanishi |

(56) References Cited

U.S. PATENT DOCUMENTS

| | | |
|---|---|---|
| 8,149,274 B2 | 4/2012 | Yamazaki |
| 8,152,718 B2 | 4/2012 | Cheng |
| 8,152,821 B2 | 4/2012 | Gambale |
| 8,157,798 B2 | 4/2012 | Takahashi |
| 8,164,836 B2 | 4/2012 | Uzawa |
| 8,167,791 B2 | 5/2012 | Tanaka |
| 8,167,795 B2 | 5/2012 | Hoeg |
| 8,167,796 B2 | 5/2012 | Negishi |
| 8,182,419 B2 | 5/2012 | Kohno |
| 8,187,171 B2 | 5/2012 | Irion |
| 8,187,174 B2 | 5/2012 | Wang |
| 8,189,041 B2 | 5/2012 | Konishi |
| 8,189,062 B2 | 5/2012 | Irion |
| 8,194,380 B2 | 6/2012 | Murata |
| 8,197,400 B2 | 6/2012 | Boutillette |
| 8,200,042 B2 | 6/2012 | Doi |
| 8,208,015 B2 | 6/2012 | Unsai |
| 8,211,009 B2 | 7/2012 | Tanaka |
| 8,212,862 B2 | 7/2012 | Kase |
| 8,212,863 B2 | 7/2012 | Tanaka |
| 8,221,309 B2 | 7/2012 | Iida |
| 8,221,311 B2 | 7/2012 | Campos |
| 8,223,198 B2 | 7/2012 | Shibasaki |
| 8,228,369 B2 | 7/2012 | Kojima |
| 8,229,549 B2 | 7/2012 | Whitman |
| 8,235,942 B2 | 8/2012 | Frassica |
| 8,248,414 B2 | 8/2012 | Gattani |
| 8,262,558 B2 | 9/2012 | Sato |
| 8,262,565 B2 | 9/2012 | Okada |
| 8,279,275 B2 | 10/2012 | Gono |
| 8,295,566 B2 | 10/2012 | Nishimura |
| 8,300,325 B2 | 10/2012 | Katahira |
| 8,310,529 B2 | 11/2012 | Krupnick |
| 8,334,900 B2 | 12/2012 | Qu |
| 8,345,092 B2 | 1/2013 | Takasaki |
| 8,348,835 B2 | 1/2013 | Fujimori |
| 8,360,960 B2 | 1/2013 | Sasaki |
| 8,360,964 B2 | 1/2013 | Ertas |
| 8,366,623 B2 | 2/2013 | Misono |
| 8,382,673 B2 | 2/2013 | Nagano |
| 8,394,013 B2 | 3/2013 | Ichimura |
| 8,394,014 B2 | 3/2013 | Fuerst |
| 8,425,405 B2 | 4/2013 | Mitani |
| 8,435,173 B2 | 5/2013 | Hosaka |
| 8,439,829 B2 | 5/2013 | Miyamoto |
| 8,444,547 B2 | 5/2013 | Miyamoto |
| 8,444,548 B2 | 5/2013 | Kumei |
| 8,449,456 B2 | 5/2013 | Ueno |
| 8,449,457 B2 | 5/2013 | Aizenfeld |
| 8,456,562 B2 | 6/2013 | Ishii |
| 8,460,182 B2 | 6/2013 | Ouyang |
| 8,465,421 B2 | 6/2013 | Finkman |
| 8,480,670 B2 | 7/2013 | Sugita |
| 8,491,467 B2 | 7/2013 | Miyamoto |
| 8,520,919 B2 | 8/2013 | Stepp |
| 8,523,764 B2 | 9/2013 | Hatcher |
| 8,523,766 B2 | 9/2013 | Kudoh |
| 8,764,642 B2 | 7/2014 | Bendele |
| 9,144,373 B2 | 9/2015 | Kaye |
| 2002/0007110 A1 | 1/2002 | Irion |
| 2002/0087047 A1 | 7/2002 | Remijan |
| 2002/0098732 A1 | 7/2002 | Shimizu |
| 2002/0109771 A1 | 8/2002 | Ledbetter |
| 2002/0109774 A1 | 8/2002 | Meron |
| 2002/0151768 A1 | 10/2002 | Akiba |
| 2002/0161281 A1 | 10/2002 | Jaffe |
| 2002/0161282 A1 | 10/2002 | Fulghum |
| 2002/0183591 A1 | 12/2002 | Matsuura |
| 2003/0030918 A1 | 2/2003 | Murayama |
| 2003/0032860 A1 | 2/2003 | Avni |
| 2003/0036681 A1 | 2/2003 | Aviv |
| 2003/0055314 A1 | 3/2003 | Petitto |
| 2003/0083552 A1 | 5/2003 | Remijan |
| 2003/0125788 A1 | 7/2003 | Long |
| 2003/0130564 A1 | 7/2003 | Martone |
| 2003/0139648 A1 | 7/2003 | Foley |
| 2003/0158462 A1 | 8/2003 | Takase |
| 2003/0181787 A1 | 9/2003 | Kondo |
| 2003/0199860 A1 | 10/2003 | Loeb |
| 2004/0015049 A1 | 1/2004 | Zaar |
| 2004/0019347 A1 | 1/2004 | Sakurai |
| 2004/0024290 A1 | 2/2004 | Root |
| 2004/0034311 A1 | 2/2004 | Mihalcik |
| 2004/0073120 A1 | 4/2004 | Motz |
| 2004/0092794 A1 | 5/2004 | Chin et al. |
| 2004/0104999 A1 | 6/2004 | Okada |
| 2004/0111012 A1 | 6/2004 | Whitman |
| 2004/0133076 A1 | 7/2004 | Kobayashi |
| 2004/0138532 A1 | 7/2004 | Glukhovsky |
| 2004/0143162 A1 | 7/2004 | Krattiger |
| 2004/0158129 A1 | 8/2004 | Okada |
| 2004/0160682 A1 | 8/2004 | Miyano |
| 2004/0176661 A1 | 9/2004 | Futatsugi |
| 2004/0190159 A1 | 9/2004 | Hasegawa |
| 2004/0210113 A1 | 10/2004 | Hasegawa |
| 2004/0220451 A1 | 11/2004 | Gravenstein |
| 2004/0242958 A1 | 12/2004 | Fujikawa |
| 2004/0242961 A1 | 12/2004 | Bughici |
| 2004/0249247 A1 | 12/2004 | Iddan |
| 2004/0254423 A1 | 12/2004 | Wendlandt |
| 2004/0260151 A1 | 12/2004 | Akiba |
| 2004/0267093 A1 | 12/2004 | Miyagi |
| 2005/0020876 A1 | 1/2005 | Shioda |
| 2005/0027164 A1 | 2/2005 | Barbato |
| 2005/0038317 A1 | 2/2005 | Ratnakar |
| 2005/0038318 A1 | 2/2005 | Goldwasser |
| 2005/0043583 A1 | 2/2005 | Killmann |
| 2005/0080342 A1 | 4/2005 | Gilreath |
| 2005/0090709 A1 | 4/2005 | Okada |
| 2005/0096501 A1 | 5/2005 | Stelzer |
| 2005/0154255 A1 | 7/2005 | Jacobs |
| 2005/0154262 A1 | 7/2005 | Banik |
| 2005/0182295 A1 | 8/2005 | Soper |
| 2005/0203338 A1 | 9/2005 | Couvillon |
| 2005/0234296 A1 | 10/2005 | Saadat |
| 2005/0234347 A1 | 10/2005 | Yamataka |
| 2005/0251127 A1 | 11/2005 | Brosch |
| 2005/0256376 A1 | 11/2005 | Bar-Or |
| 2005/0261553 A1 | 11/2005 | Swain |
| 2005/0272975 A1 | 12/2005 | McWeeney |
| 2005/0283048 A1 | 12/2005 | Gill |
| 2005/0284491 A1 | 12/2005 | Tashiro |
| 2006/0004257 A1 | 1/2006 | Gilad |
| 2006/0047184 A1 | 3/2006 | Banik |
| 2006/0052663 A1 | 3/2006 | Koitabashi |
| 2006/0063976 A1 | 3/2006 | Aizenfeld |
| 2006/0069307 A1 | 3/2006 | Boulais |
| 2006/0069314 A1 | 3/2006 | Farr |
| 2006/0149129 A1 | 7/2006 | Watts |
| 2006/0173244 A1 | 8/2006 | Boulais |
| 2006/0183971 A1 | 8/2006 | Haviv |
| 2006/0183975 A1 | 8/2006 | Saadat |
| 2006/0189845 A1 | 8/2006 | Maahs |
| 2006/0211916 A1 | 9/2006 | Kasahara |
| 2006/0217594 A1 | 9/2006 | Ferguson |
| 2006/0224040 A1 | 10/2006 | Khait |
| 2006/0229499 A1 | 10/2006 | Eisenkolb |
| 2006/0241347 A1 | 10/2006 | Whitehead |
| 2006/0252994 A1 | 11/2006 | Ratnakar |
| 2006/0264704 A1 | 11/2006 | Fujimori |
| 2006/0293556 A1 | 12/2006 | Garner |
| 2006/0293562 A1 | 12/2006 | Uchimura |
| 2007/0015964 A1 | 1/2007 | Eversull |
| 2007/0015968 A1 | 1/2007 | Shelnutt |
| 2007/0019916 A1 | 1/2007 | Takami |
| 2007/0020694 A1 | 1/2007 | Pickford |
| 2007/0030345 A1 | 2/2007 | Amling |
| 2007/0049803 A1 | 3/2007 | Moriyama |
| 2007/0055100 A1 | 3/2007 | Kato |
| 2007/0073109 A1 | 3/2007 | Irion |
| 2007/0078304 A1 | 4/2007 | Shimizu |
| 2007/0083081 A1 | 4/2007 | Schlagenhauf |
| 2007/0100206 A1 | 5/2007 | Lin |
| 2007/0106119 A1 | 5/2007 | Hirata |

(56) References Cited

U.S. PATENT DOCUMENTS

| | | |
|---|---|---|
| 2007/0115376 A1 | 5/2007 | Igarashi |
| 2007/0118019 A1 | 5/2007 | Mitani |
| 2007/0123748 A1 | 5/2007 | Meglan |
| 2007/0142711 A1 | 6/2007 | Bayer |
| 2007/0162095 A1 | 7/2007 | Kimmel |
| 2007/0167673 A1 | 7/2007 | Enomoto |
| 2007/0167681 A1 | 7/2007 | Gill |
| 2007/0173686 A1 | 7/2007 | Lin |
| 2007/0173687 A1 | 7/2007 | Shima |
| 2007/0177008 A1 | 8/2007 | Bayer |
| 2007/0177009 A1 | 8/2007 | Bayer |
| 2007/0185384 A1 | 8/2007 | Bayer |
| 2007/0197875 A1 | 8/2007 | Osaka |
| 2007/0203396 A1 | 8/2007 | McCutcheon et al. |
| 2007/0206945 A1 | 9/2007 | DeLorme |
| 2007/0208225 A1 | 9/2007 | Czaniera |
| 2007/0213590 A1 | 9/2007 | Squicciarini |
| 2007/0213591 A1 | 9/2007 | Aizenfeld |
| 2007/0225556 A1 | 9/2007 | Ortiz |
| 2007/0225565 A1 | 9/2007 | Ogino |
| 2007/0229656 A1 | 10/2007 | Khait |
| 2007/0244353 A1 | 10/2007 | Larsen |
| 2007/0244362 A1 | 10/2007 | El-Hachem |
| 2007/0244366 A1 | 10/2007 | Murata |
| 2007/0246506 A1 | 10/2007 | Hamazaki |
| 2007/0249899 A1 | 10/2007 | Seifert |
| 2007/0265498 A1 | 11/2007 | Ito |
| 2007/0282165 A1 | 12/2007 | Hopkins |
| 2007/0293720 A1 | 12/2007 | Bayer |
| 2008/0009672 A1 | 1/2008 | Krattiger |
| 2008/0021274 A1 | 1/2008 | Bayer |
| 2008/0021281 A1 | 1/2008 | Fujimori |
| 2008/0039689 A1 | 2/2008 | Yoshimitsu |
| 2008/0039693 A1 | 2/2008 | Karasawa |
| 2008/0045797 A1 | 2/2008 | Yasushi |
| 2008/0051628 A1 | 2/2008 | Pecherer |
| 2008/0051629 A1 | 2/2008 | Sugiyama |
| 2008/0051655 A1 | 2/2008 | Sato |
| 2008/0058595 A1 | 3/2008 | Snoke |
| 2008/0058598 A1 | 3/2008 | Ries |
| 2008/0058601 A1 | 3/2008 | Fujimori |
| 2008/0064931 A1 | 3/2008 | Schena |
| 2008/0065127 A1 | 3/2008 | Adams |
| 2008/0071290 A1 | 3/2008 | Larkin |
| 2008/0100699 A1 | 5/2008 | Hibi |
| 2008/0130108 A1 | 6/2008 | Bayer |
| 2008/0139881 A1 | 6/2008 | Cover |
| 2008/0163652 A1 | 7/2008 | Shatskin |
| 2008/0167529 A1 | 7/2008 | Otawara |
| 2008/0171910 A1 | 7/2008 | Kanazawa |
| 2008/0177139 A1 | 7/2008 | Courtney |
| 2008/0177140 A1 | 7/2008 | Cline |
| 2008/0221388 A1 | 7/2008 | Courtney |
| 2008/0188715 A1 | 8/2008 | Fujimoto |
| 2008/0225134 A1 | 9/2008 | Amling |
| 2008/0255425 A1 | 10/2008 | Voegele |
| 2008/0262302 A1 | 10/2008 | Azarbarzin |
| 2008/0262312 A1 | 10/2008 | Carroll |
| 2008/0275298 A1 | 11/2008 | Ratnakar |
| 2008/0312497 A1 | 12/2008 | Elmouelhi |
| 2009/0005643 A1 | 1/2009 | Smith |
| 2009/0054790 A1 | 2/2009 | Czaniera |
| 2009/0062615 A1 | 3/2009 | Yamaya |
| 2009/0067067 A1 | 3/2009 | Yamaya |
| 2009/0086017 A1 | 4/2009 | Miyano |
| 2009/0093679 A1 | 4/2009 | Suigetsu |
| 2009/0118577 A9 | 5/2009 | Snay |
| 2009/0137869 A1 | 5/2009 | Soutorine |
| 2009/0147076 A1 | 6/2009 | Ertas |
| 2009/0161234 A1 | 6/2009 | Sasamoto |
| 2009/0163769 A1 | 6/2009 | Robertson |
| 2009/0209811 A1 | 8/2009 | Higuchi |
| 2009/0216084 A1 | 8/2009 | Yamane |
| 2009/0231419 A1 | 9/2009 | Bayer |
| 2009/0247831 A1 | 10/2009 | Miyamoto |
| 2009/0253966 A1 | 10/2009 | Ichimura |
| 2009/0259097 A1 | 10/2009 | Thompson |
| 2009/0259102 A1 | 10/2009 | Koninckx |
| 2009/0268011 A1 | 10/2009 | Scott |
| 2009/0284649 A1 | 11/2009 | Pease |
| 2009/0287047 A1 | 11/2009 | Onoda |
| 2009/0287192 A1 | 11/2009 | Vivenzio |
| 2009/0290236 A1 | 11/2009 | Wang |
| 2009/0299144 A1 | 12/2009 | Shigemori |
| 2009/0306474 A1 | 12/2009 | Wilson |
| 2009/0306476 A1 | 12/2009 | Banik |
| 2009/0318757 A1 | 12/2009 | Singh |
| 2010/0010301 A1 | 1/2010 | Hale |
| 2010/0010302 A1 | 1/2010 | Hadani |
| 2010/0013914 A1 | 1/2010 | Bettesh |
| 2010/0016673 A1 | 1/2010 | Bandy |
| 2010/0030020 A1 | 2/2010 | Sanders |
| 2010/0042097 A1 | 2/2010 | Newton |
| 2010/0047733 A1 | 2/2010 | Nahlieli |
| 2010/0053312 A1 | 3/2010 | Watanabe |
| 2010/0073470 A1 | 3/2010 | Takasaki |
| 2010/0076268 A1* | 3/2010 | Takasugi ............ A61B 1/00183 600/171 |
| 2010/0081874 A1 | 4/2010 | Miyamoto |
| 2010/0081875 A1 | 4/2010 | Fowler |
| 2010/0087706 A1 | 4/2010 | Syed |
| 2010/0121142 A1 | 5/2010 | Ouyang |
| 2010/0123950 A1 | 5/2010 | Fujiwara |
| 2010/0130822 A1 | 5/2010 | Katayama |
| 2010/0137682 A1 | 6/2010 | Doguchi |
| 2010/0137687 A1 | 6/2010 | Schwartz |
| 2010/0141746 A1 | 6/2010 | Ikeda |
| 2010/0152612 A1 | 6/2010 | Headley |
| 2010/0160729 A1 | 6/2010 | Smith |
| 2010/0174144 A1 | 7/2010 | Hsu |
| 2010/0185056 A1 | 7/2010 | Gordon |
| 2010/0187408 A1 | 7/2010 | Klem |
| 2010/0201985 A1 | 8/2010 | Wang |
| 2010/0204609 A1 | 8/2010 | Worth |
| 2010/0217076 A1 | 8/2010 | Ratnakar |
| 2010/0217081 A1 | 8/2010 | Deppmeier |
| 2010/0228086 A1 | 9/2010 | Ohki |
| 2010/0245653 A1 | 9/2010 | Bodor |
| 2010/0249496 A1 | 9/2010 | Cardenas |
| 2010/0249513 A1 | 9/2010 | Tydlaska |
| 2010/0256447 A1 | 10/2010 | Dubi |
| 2010/0286475 A1 | 11/2010 | Robertson |
| 2010/0296178 A1 | 11/2010 | Genet |
| 2010/0298640 A1 | 11/2010 | Oneda |
| 2010/0298773 A1 | 11/2010 | Nitsan |
| 2010/0305503 A1 | 12/2010 | Fang |
| 2010/0317919 A1 | 12/2010 | Takaoka |
| 2010/0317921 A1 | 12/2010 | Marple |
| 2010/0318061 A1 | 12/2010 | Derrick |
| 2010/0326703 A1 | 12/2010 | Gilad |
| 2011/0028790 A1 | 2/2011 | Farr |
| 2011/0054256 A1 | 3/2011 | Cushner |
| 2011/0112363 A1 | 5/2011 | Koga |
| 2011/0160530 A1 | 6/2011 | Ratnakar |
| 2011/0169931 A1 | 7/2011 | Pascal |
| 2011/0184243 A1 | 7/2011 | Wright |
| 2011/0196200 A1 | 8/2011 | Glozman |
| 2011/0196204 A1 | 8/2011 | Setty |
| 2011/0211267 A1 | 9/2011 | Takato |
| 2011/0224487 A1 | 9/2011 | Ogawa |
| 2011/0245600 A1 | 10/2011 | Ishii |
| 2011/0245609 A1 | 10/2011 | Laser |
| 2011/0257478 A1 | 10/2011 | Kleiner |
| 2011/0263938 A1 | 10/2011 | Levy |
| 2011/0282144 A1 | 11/2011 | Gettman |
| 2011/0282148 A1 | 11/2011 | Kase |
| 2011/0288374 A1 | 11/2011 | Hadani |
| 2011/0295061 A1 | 12/2011 | Haramaty |
| 2011/0295062 A1 | 12/2011 | GratacosSolsona |
| 2011/0295064 A1 | 12/2011 | Kagawa |
| 2011/0306832 A1 | 12/2011 | Bassan |
| 2011/0313249 A1 | 12/2011 | Viola |
| 2012/0010465 A1 | 1/2012 | Erikawa |
| 2012/0029291 A1 | 2/2012 | Wallace |

(56) References Cited

U.S. PATENT DOCUMENTS

| | | |
|---|---|---|
| 2012/0040305 A1 | 2/2012 | Karazivan |
| 2012/0041534 A1 | 2/2012 | Clerc |
| 2012/0046524 A1 | 2/2012 | Miyamoto |
| 2012/0053407 A1 | 3/2012 | Levy |
| 2012/0057251 A1 | 3/2012 | Takato |
| 2012/0065468 A1 | 3/2012 | Levy |
| 2012/0071748 A1 | 3/2012 | Mark |
| 2012/0078042 A1 | 3/2012 | Uram |
| 2012/0088965 A1 | 4/2012 | Stokes |
| 2012/0095391 A1 | 4/2012 | Bendele |
| 2012/0104230 A1 | 5/2012 | Eismann |
| 2012/0178995 A1 | 7/2012 | Newton |
| 2012/0209062 A1 | 8/2012 | Qiao |
| 2012/0229615 A1 | 9/2012 | Kirma |
| 2012/0232340 A1 | 9/2012 | Levy |
| 2012/0232342 A1 | 9/2012 | Reydel |
| 2012/0232343 A1 | 9/2012 | Levy |
| 2012/0253121 A1 | 10/2012 | Kitano |
| 2012/0253284 A1 | 10/2012 | Nitsan |
| 2012/0259175 A1 | 10/2012 | Reydel |
| 2012/0265094 A1 | 10/2012 | Goldfarb |
| 2013/0012778 A1 | 1/2013 | Bayer |
| 2013/0012794 A1 | 1/2013 | Zeng |
| 2013/0060086 A1 | 3/2013 | Talbert |
| 2013/0109916 A1 | 5/2013 | Levy |
| 2013/0109918 A1 | 5/2013 | Pagan |
| 2013/0110003 A1 | 5/2013 | Surti |
| 2013/0131445 A1 | 5/2013 | Zerfas |
| 2013/0131447 A1 | 5/2013 | Benning |
| 2013/0131454 A1 | 5/2013 | McCormack |
| 2013/0137930 A1 | 5/2013 | Menabde |
| 2013/0172670 A1 | 7/2013 | Levy |
| 2013/0172673 A1 | 7/2013 | Kennedy |
| 2013/0172674 A1 | 7/2013 | Kennedy |
| 2013/0172677 A1 | 7/2013 | Kennedy |
| 2013/0172678 A1 | 7/2013 | Kennedy |
| 2013/0190561 A1 | 7/2013 | Oskin |
| 2013/0194404 A1 | 8/2013 | Christiansen |
| 2013/0204088 A1 | 8/2013 | Miyamoto |
| 2013/0253272 A1 | 9/2013 | Takahashi |
| 2013/0267778 A1 | 10/2013 | Rehe |
| 2013/0296649 A1 | 11/2013 | Kirma |
| 2013/0314521 A1 | 11/2013 | Satake |
| 2013/0317295 A1 | 11/2013 | Morse |
| 2014/0364691 A1 | 12/2014 | Krivopisk |

FOREIGN PATENT DOCUMENTS

| | | |
|---|---|---|
| CN | 1988841 | 6/2007 |
| CN | 2936129 Y | 8/2007 |
| CN | 101061940 A | 10/2007 |
| CN | 201108422 Y | 9/2008 |
| CN | 101385633 A | 3/2009 |
| CN | 101396258 | 4/2009 |
| CN | 101926171 | 12/2010 |
| CN | 102058375 A | 5/2011 |
| CN | 102058380 A | 5/2011 |
| CN | 101061940 | 6/2011 |
| CN | 201870615 U | 6/2011 |
| CN | 102469924 | 5/2012 |
| DE | 102005008153 A1 | 11/2005 |
| EP | 0029555 A2 | 6/1981 |
| EP | 543738 A1 | 5/1993 |
| EP | 730844 | 9/1996 |
| EP | 1195630 A2 | 4/2002 |
| EP | 1325458 | 7/2003 |
| EP | 1347702 A2 | 10/2003 |
| EP | 948283 B1 | 4/2004 |
| EP | 1535565 | 6/2005 |
| EP | 1073365 B1 | 7/2005 |
| EP | 1627595 A1 | 2/2006 |
| EP | 668738 B1 | 6/2006 |
| EP | 1685790 A1 | 8/2006 |
| EP | 1472972 B1 | 10/2006 |
| EP | 1790280 A1 | 5/2007 |
| EP | 1834572 A1 | 9/2007 |
| EP | 1952750 | 8/2008 |
| EP | 1977675 | 10/2008 |
| EP | 1977682 A2 | 10/2008 |
| EP | 1974000653 | 10/2008 |
| EP | 1992292 A1 | 11/2008 |
| EP | 2022389 A1 | 2/2009 |
| EP | 2144571 A2 | 1/2010 |
| EP | 2276389 A1 | 1/2011 |
| EP | 1835847 B1 | 5/2011 |
| EP | 1870014 B1 | 1/2012 |
| EP | 2501271 A1 | 9/2012 |
| EP | 2503933 A1 | 10/2012 |
| EP | 2512577 A2 | 10/2012 |
| EP | 2529660 A1 | 12/2012 |
| EP | 2596756 A1 | 5/2013 |
| EP | 2623019 A1 | 8/2013 |
| GB | 2321132 | 7/1998 |
| GB | 2352922 A | 2/2001 |
| JP | 2010279539 | 12/1920 |
| JP | S5551270 | 5/1980 |
| JP | 55078932 | 6/1980 |
| JP | 61055657 | 11/1986 |
| JP | S6296616 | 6/1987 |
| JP | 6359332 | 11/1988 |
| JP | H0253701 | 4/1990 |
| JP | H02188709 A | 7/1990 |
| JP | H03116801 | 5/1991 |
| JP | H04341232 | 11/1992 |
| JP | 5049000594 | 3/1993 |
| JP | H05309069 | 11/1993 |
| JP | 6105000800 | 4/1994 |
| JP | 7000000352 | 1/1995 |
| JP | 8122000657 | 5/1996 |
| JP | H09 294709 A | 11/1997 |
| JP | H09 313435 A | 12/1997 |
| JP | 1013007179 | 4/1998 |
| JP | 1015001113 | 6/1998 |
| JP | 11125773 | 5/1999 |
| JP | 11137512 | 5/1999 |
| JP | H11125773 | 5/1999 |
| JP | H11125773 A | 5/1999 |
| JP | 1116009340 | 6/1999 |
| JP | 1116009341 | 6/1999 |
| JP | H11253401 | 9/1999 |
| JP | 2000171727 A | 6/2000 |
| JP | 2000325306 | 11/2000 |
| JP | 2000330015 A | 11/2000 |
| JP | 2001061762 | 3/2001 |
| JP | 2001198086 | 7/2001 |
| JP | 2002000559 | 1/2002 |
| JP | 2002017667 | 1/2002 |
| JP | 2002058636 | 2/2002 |
| JP | 200265589 A | 3/2002 |
| JP | 2002065575 | 3/2002 |
| JP | 2002078675 | 3/2002 |
| JP | 2002216902 | 8/2002 |
| JP | 2002291693 | 10/2002 |
| JP | 2003 033324 A | 2/2003 |
| JP | 2003038431 | 2/2003 |
| JP | 2003061900 | 3/2003 |
| JP | 2003111724 | 4/2003 |
| JP | 2003190082 | 7/2003 |
| JP | 2003220017 | 8/2003 |
| JP | 2003245247 | 9/2003 |
| JP | 2004022391 | 1/2004 |
| JP | 2004049754 | 2/2004 |
| JP | 2004049756 | 2/2004 |
| JP | 2004129834 | 4/2004 |
| JP | 2004205779 A | 7/2004 |
| JP | 2004354888 A | 12/2004 |
| JP | 2005013557 A | 1/2005 |
| JP | 2005058547 | 3/2005 |
| JP | 2005253543 | 9/2005 |
| JP | 2005323874 A | 11/2005 |
| JP | 2006003549 A | 1/2006 |
| JP | 3765500 | 2/2006 |
| JP | 2006068109 | 3/2006 |
| JP | 2006068109 A | 3/2006 |

(56) References Cited

FOREIGN PATENT DOCUMENTS

| | | |
|---|---|---|
| JP | 2006218155 | 8/2006 |
| JP | 2006280954 | 10/2006 |
| JP | 2006288758 | 10/2006 |
| JP | 2007020866 A | 2/2007 |
| JP | 2007185276 | 7/2007 |
| JP | 2008068025 | 3/2008 |
| JP | 2008118568 | 5/2008 |
| JP | 2008161569 A | 7/2008 |
| JP | 2008229204 | 10/2008 |
| JP | 2008257108 A | 10/2008 |
| JP | 2009233186 | 10/2009 |
| JP | 2009251574 | 10/2009 |
| JP | 4445647 | 4/2010 |
| JP | 2010178766 A | 8/2010 |
| WO | 9219148 A1 | 11/1992 |
| WO | 00052643 A1 | 9/2000 |
| WO | 2002045595 | 6/2002 |
| WO | 2004026125 | 4/2004 |
| WO | 2005082228 A1 | 9/2005 |
| WO | 2006073581 | 7/2006 |
| WO | 2006105932 A1 | 10/2006 |
| WO | 2007113801 A2 | 10/2007 |
| WO | 2007087421 | 11/2007 |
| WO | 2007136859 A2 | 11/2007 |
| WO | 2008012813 A1 | 1/2008 |
| WO | 2008073243 | 6/2008 |
| WO | 2008093288 | 8/2008 |
| WO | 2008139770 | 11/2008 |
| WO | 2008155776 | 12/2008 |
| WO | 2008156623 | 12/2008 |
| WO | 2009009414 | 1/2009 |
| WO | 2009025843 | 2/2009 |
| WO | 2009040744 | 4/2009 |
| WO | 2009095915 | 8/2009 |
| WO | 2010021342 | 2/2010 |
| WO | 2010028612 | 3/2010 |
| WO | 2010045406 | 4/2010 |
| WO | 2010064506 | 6/2010 |
| WO | 2010066788 | 6/2010 |
| WO | 2010146587 A1 | 12/2010 |
| WO | 2011008922 | 1/2011 |
| WO | 2011041724 | 4/2011 |
| WO | 2011083451 | 7/2011 |
| WO | 2011126812 | 10/2011 |
| WO | 2012038958 | 3/2012 |
| WO | 2013131578 | 3/2012 |
| WO | 2012056453 A2 | 5/2012 |
| WO | 2012077116 | 6/2012 |
| WO | 2012077117 A1 | 6/2012 |
| WO | 2012088201 A2 | 6/2012 |
| WO | 2012103266 | 8/2012 |
| WO | 2012120507 A1 | 9/2012 |
| WO | 2012153324 | 11/2012 |
| WO | 2013014673 | 1/2013 |
| WO | 2013024476 | 2/2013 |
| WO | 2013043704 | 3/2013 |
| WO | 2013128136 | 9/2013 |
| WO | 2013144944 | 10/2013 |
| WO | 2014061023 | 4/2014 |

OTHER PUBLICATIONS

Corrected European Search Opinion for EP14186113.8, Apr. 29, 2015.
Extended European Search Report for EP11847191.1, Jan. 15, 2016.
Examination Report for Canadian Patent Application No. CA2765559, Jan. 18, 2016.
Examination Search Report for Canadian Patent Application No. CA2765559, Jan. 18, 2016.
Extended European Search Report for EP11846069.0, Apr. 24, 2014.
Extended European Search Report for EP12817452.1, Mar. 9, 2015.
Extended European Search Report for EP14186113.8, Apr. 1, 2015.
First Image of an Endo Smart Cap, made by Medivators, and obtained from http://www.bymemedical.com/prod/145L.jpg and advertised at http://www.medivators.com/products/endoscopy-procedure-products/irrigation-tubing/endo-smartcap%C2%AE.
First Office Action for CN 2012800171292, dated Feb. 28, 2015.
First Office Action for CN 2012800368972, Jun. 1, 2015.
First office action for CN2011800627366, Feb. 25, 2015.
International Search Report for PCT/EP2009/066726, Aug. 16, 2010.
International Search Report for PCT/IL2011/000832, May 16, 2012.
International Search Report for PCT/IL2011/050049, May 15, 2012.
International Search Report for PCT/IL2011/050050, May 16, 2012.
International Search Report for PCT/IL2012/050037, Jun. 1, 2012.
International Search Report for PCT/IL2012/050274, Nov. 15, 2012.
International Search Report for PCT/IL2012/050299, Nov. 15, 2012.
International Search Report for PCT/IL2013/050840, Feb. 2, 2014.
International Search Report of PCT/IL10/00476 mailed Sep. 27, 2010, 2 pages.
International Search Report of PCT/IL2011/000745, dated May 8, 2012.
Notice of Allowance dated Dec. 15, 2014 for U.S. Appl. No. 13/713,466.
Notice of Allowance dated Dec. 15, 2015 for U.S. Appl. No. 13/713,466.
Notice of Allowance dated Dec. 23, 2015 for U.S. Appl. No. 13/992,021.
Notice of Allowance dated Jun. 17, 2015 for U.S. Appl. No. 13/190,968.
Notice of Allowance dated Jun. 8, 2015 for U.S. Appl. No. 13/413,252.
Notice of Allowance dated Jun. 8, 2015 for U.S. Appl. No. 13/984,028.
Office Action dated Aug. 19, 2015 for U.S. Appl. No. 13/713,466.
Office Action dated Aug. 19, 2015 for U.S. Appl. No. 13/713,449.
Office Action dated Aug. 27, 2015 for U.S. Appl. No. 13/655,120.
Office Action dated Aug. 4, 2015 for U.S. Appl. No. 13/557,114.
Office Action dated Aug. 5, 2015 for U.S. Appl. No. 13/212,627.
Office Action dated Aug. 6, 2015 for U.S. Appl. No. 13/119,032.
Office Action dated Dec. 4, 2015 for U.S. Appl. No. 13/822,908.
Office Action dated Feb. 13, 2015 for U.S. Appl. No. 13/713,449.
Office Action dated Feb. 17, 2015 for U.S. Appl. No. 13/882,004.
Office Action dated Jan. 12, 2016 for U.S. Appl. No. 13/713,466.
Office Action dated Jan. 15, 2015 for U.S. Appl. No. 13/190,968.
Office Action dated Jul. 21, 2015 for U.S. Appl. No. 13/992,021.
Office Action dated Jun. 3, 2015 for U.S. Appl. No. 13/992,014.
Office Action dated Mar. 12, 2015 for U.S. Appl. No. 13/822,908.
Office Action dated Mar. 24, 2016 for U.S. Appl. No. 13/212,627.
Office Action dated Mar. 6, 2015 for U.S. Appl. No. 13/413,059.
Office Action dated May 1, 2015 for U.S. Appl. No. 13/992,021.
Office Action dated Nov. 16, 2015 for U.S. Appl. No. 13/557,114.
Office Action dated Nov. 24, 2015 for U.S. Appl. No. 13/413,059.
Office Action dated Nov. 26, 2014 for U.S. Appl. No. 13/713,466.
Office Action dated Nov. 3, 2015 for U.S. Appl. No. 13/992,014.
Office Action dated Oct. 7, 2015 for U.S. Appl. No. 13/882,004.
European Office Action in corresponding European Application No. 20185557.4, dated Jun. 27, 2023 (8 pages).
European Patent Office Extended Search Report issued in corresponding European Application No. 20185557.4, mailed Mar. 29, 2021 (9 pages).
Office Action for Chinese Patent Application No. 201180067259.2, May 29, 2015.
Office Action for Chinese Patent Application No. 201280038808.8, May 20, 2015.
Office Action for Japanese Patent Application No. 2013-535586, Sep. 24, 2015.
Office Action for Japanese Patent Application No. 2013-542668, Oct. 1, 2015.
Prosecution File History for U.S. Appl. No. 13/190,968; Jul. 26, 2011 through Jun. 17, 2015.
Second Office Action for Chinese Patent Applicatio No. CN201280038808.8, Feb. 25, 2016.

(56) References Cited

OTHER PUBLICATIONS

Second office action for Chinese Patent Application No. 201180062736.6, Oct. 12, 2015.
Supplementary European Search Report for EP11847191.1, Jan. 16, 2015.
Supplementary European Search Report for European Application No. EP12823972, May 13, 2015.
First Office Action for Chinese Patent Applicatio No. CN201380053351.2, Mar. 2, 2016.
Office Action dated Mar. 23, 2016 for U.S. Appl. No. 13/713,449.
Office Action dated Mar. 28, 2016 for U.S. Appl. No. 13/119,032.
Office Action for Japanese Patent Application No. JP2014-522214, dated Apr. 26, 2016.
Office Action for Japanese Patent Application No. JP2014-525562, dated Apr. 26, 2016.
Second image of an Endo Smart Cap, made by Medivators, and obtained from http://www.bymemedical.com/prod/150L.jpg and advertised at http://www.medivators.com/products/endoscopy-procedure-products/irrigation-tubing/endo-smartcap%C2%AE.
Notice of Allowance dated Aug. 26, 2016 for U.S. Appl. No. 13/212,627.
Office Action dated Jun. 30, 2016 for U.S. Appl. No. 13/655,120.
Second Office Action for Chinese Patent Application No. 201180067259.2, Mar. 30, 2016.
Extended European Search Report for application No. EP12755186, completed on May 23, 2016.
Supplementary European Search Report for EP13847670, completed on May 19, 2016.
Office Action dated Apr. 28, 2016 for U.S. Appl. No. 13/992,014.
Office Action dated Sep. 16, 2016 for U.S. Appl. No. 13/992,014.
Notice of Allowance dated Oct. 12, 2016 for U.S. Appl. No. 13/119,032.
Office Action dated Oct. 7, 2016 for U.S. Appl. No. 13/713,449.
Notice of Allowance dated Nov. 9, 2016 for U.S. Appl. No. 13/557,114.
Third Office Action for Chinese Patent Application No. 201180067259.2, Oct. 21, 2016.
Office Action for Chinese Patent Application No. 201180062736.6, Dec. 23, 2016.
Office Action for Japanese Patent Application No. 2016-105009, Jan. 16, 2017.
Office Action for Chinese Patent Application No. 201380053351.2, Dec. 13, 2016.
First Office Action for EP11847191.1, Feb. 21, 2017.
Office Action dated Mar. 21, 2017 for U.S. Appl. No. 13/992,014.
Notice of Allowance dated Apr. 18, 2017 for U.S. Appl. No. 13/713,449.
Examination Report for EP11846069.0, Feb. 21, 2017.
Extended European Search Report for EP11826512.3, Apr. 6, 2017.
Office Action dated May 23, 2017 for U.S. Appl. No. 13/655,120.

\* cited by examiner

MULTI-VIEWING ELEMENT ENDOSCOPE

CROSS REFERENCE TO RELATED APPLICATIONS

This application is a continuation of U.S. Nonprovisional patent application Ser. No. 17/669,757, filed Feb. 11, 2022, which is a continuation of U.S. Nonprovisional patent application Ser. No. 16/567,333, filed Sep. 11, 2019, now U.S. Pat. No. 11,278,190, issued Mar. 22, 2022, which is a continuation of U.S. Nonprovisional patent application Ser. No. 15/275,417, filed Sep. 25, 2016, now U.S. Pat. No. 10,799,095, issued Oct. 13, 2020, which is a continuation of U.S. Nonprovisional patent application Ser. No. 13/212,627, filed Aug. 18, 2011, now U.S. Pat. No. 9,492,063, issued Nov. 15, 2016, which is a continuation-in-part (CIP) of U.S. patent application Ser. No. 13/119,032, filed Jul. 15, 2011, now U.S. Pat. No. 9,554,692, filed Jan. 31, 2017, which is the U.S. national stage entry under 35 U.S.C. § 371 of PCT International Patent Application No. PCT/IL2010/000476, filed Jun. 16, 2010, which claims the benefit of U.S. Provisional Patent Application No. 61/218,085, filed Jun. 18, 2009. Each of the above-mentioned applications is herein incorporated by reference in its entirety.

FIELD

Embodiments of the disclosure relate to a multi-viewing elements endoscope.

BACKGROUND

Endoscopes have attained great acceptance within the medical community, since they provide a means for performing procedures with minimal patient trauma, while enabling the physician to view the internal anatomy of the patient. Over the years, numerous endoscopes have been developed and categorized according to specific applications, such as cystoscopy, colonoscopy, laparoscopy, upper GI endoscopy and others. Endoscopes may be inserted into the body's natural orifices or through an incision in the skin.

An endoscope is usually an elongated tubular shaft, rigid or flexible, having a video camera or a fiber optic lens assembly at its distal end. The shaft is connected to a handle, which sometimes includes an ocular for direct viewing. Viewing is also usually possible via an external screen. Various surgical tools may be inserted through a working channel in the endoscope for performing different surgical procedures.

Among the disadvantages of existing endoscopes, are their limited field of view and their complicated packing of all the required elements, such as electronics and together with fluid carrying elements in the small sized endoscope tip section.

There is thus a need in the art for endoscopes, such as colonoscopies, that allow a broader field of view and also enable the function of all necessary elements in the tip section.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, according to some embodiments, a tip section of a multi-viewing elements endoscope, the tip section comprising: a front-pointing viewing element and a discrete front illuminator associated therewith; a front fluid injector configured for cleaning at least one of said front-pointing viewing element and/or said discrete front illuminator; a side-pointing viewing element; a working channel configured for insertion of a surgical tool; and a pathway fluid injector for inflating and/or cleaning a body cavity into which the endoscope is inserted.

According to some embodiments, the term "viewing element" may include a camera. According to additional or alternative embodiments, the term "viewing element" may include a fiber optic lens assembly. The fiber optic lens assembly may include one or more lenses located at the tip section of the endoscope and fiber optic associated to the one or more lenses and configured to receive light from an area of interest (tested/examined area, such as a colon of a subject) and transfer the received light to a (video) camera which may be located in the handle of the endoscope or in the console associated with the endoscope.

There is provided, according to some embodiments, a multi-viewing element endoscope comprising: an elongated shaft terminating with a tip section turnable by way of a bending section, wherein said tip section comprises: a front-pointing viewing element and a discrete front illuminator associated therewith; a front fluid injector configured for cleaning at least one of said front-pointing viewing element and/or said discrete front illuminator; a side-pointing viewing element; a working channel configured for insertion of a surgical tool; and a pathway fluid injector for inflating and/or cleaning a body cavity into which the endoscope is inserted.

The tip section may further include a discrete side illuminator associated with side-pointing viewing element. The tip section may further include a side fluid injector configured for cleaning said side-pointing viewing element and/or said discrete side illuminator.

There is provided, according to an embodiment, a multi-viewing element endoscope comprising: an elongated shaft terminating with a tip section turnable by way of a bending section, wherein said tip section comprises: a front-pointing viewing element and a discrete front illuminator associated therewith; a front fluid injector configured for cleaning at least one of said front-pointing viewing element and said discrete front illuminator; a side-pointing viewing element and a discrete side illuminator associated therewith; a side fluid injector configured for cleaning at least one of said side-pointing viewing element and said discrete side illuminator; a working channel configured for insertion of a surgical tool; and a pathway fluid injector for inflating and/or cleaning a body cavity into which the endoscope is inserted.

There is further provided, according to an embodiment, a multi-viewing element endoscopy system comprising: an endoscope comprising a handle and an elongated shaft terminating with a tip section turnable by way of a bending section, wherein said tip section comprises: a front-pointing viewing element and a discrete front illuminator associated therewith, a front fluid injector configured for cleaning at least one of said front-pointing viewing element and said discrete front illuminator, a side-pointing viewing element and a discrete side illuminator associated therewith, a side fluid injector configured for cleaning at least one of said side-pointing viewing element and said discrete side illuminator, a working channel configured for insertion of a surgical tool, and a pathway fluid injector for inflating and/or cleaning a body cavity into which the endoscope is inserted;

a controller connected to said handle of said endoscope by way of a utility cable; and a display connected to said controller and configured to display video streams received from said front and side-pointing viewing elements.

In some embodiments, the front-pointing viewing element, the side-pointing viewing element or both comprise fiber optic lens assembly. In some embodiments, the front-pointing viewing element comprises a camera and the side-pointing viewing element comprises a fiber optic lens assembly. In some embodiments, the front-pointing viewing element comprises a fiber optic lens assembly and the side-pointing viewing element comprises a camera.

In some embodiments, the fiber optic lens assembly is configured to receive light from an area of interest and to transfer the received light to a camera located outside said tip section. The camera may be located in a handle of said endoscope or in a console associated with said endoscope.

In some embodiments, said front-pointing viewing element and said side-pointing viewing element are pointing at directions essentially perpendicular to one another.

In some embodiments, said front-pointing viewing element and said side-pointing viewing element are pointing approximately 100 to 145 degrees relative to one another.

In some embodiments, a center of said side-pointing viewing element is positioned approximately 7 to 11 millimeters from a distal end of said tip section.

In some embodiments, each of said discrete front and side illuminators comprises one or more light-emitting diodes (LED).

In some embodiments, at least one of said discrete front and side illuminators is configured to emit white light.

In some embodiments, at least one of said discrete front and side illuminators is configured to emit ultraviolet light.

In some embodiments, at least one of said discrete front and side illuminators is configured to emit infrared light.

In some embodiments, at least one of said discrete front and side illuminators is configured to emit near-infrared light.

In some embodiments, said discrete front and side illuminators are configured to emit light in different wavelengths.

In some embodiments, said tip section further comprises an additional discrete front illuminator configured to emit light having a different wavelength than said discrete front illuminator.

In some embodiments, said additional discrete front illuminator and said discrete front illuminator are configured to simultaneously emit light, each at a different wavelength.

In some embodiments, said tip section further comprises an additional discrete side illuminator configured to emit light having a different wavelength than said discrete side illuminator.

In some embodiments, said additional discrete side illuminator and said discrete side illuminator are configured to simultaneously emit light, each at a different wavelength.

In some embodiments, any one of the front-pointing camera and/or the side-pointing camera comprises a Charge Coupled Device (CCD) or a Complementary Metal Oxide Semiconductor (CMOS) image sensor.

In some embodiments, said front and side fluid injectors are connected to a same fluid supply channel.

In some embodiments, said pathway fluid injector is connected to said fluid supply channel, together with said front and side fluid injectors.

In some embodiments, at least one of said front and side-pointing viewing elements comprises a lens assembly providing a field of view of 90 degrees or more.

In some embodiments, at least one of said front and side-pointing viewing elements comprises a lens assembly providing a field of view of 120 degrees or more.

In some embodiments, at least one of said front and side-pointing viewing elements comprises a lens assembly providing a field of view of 150 degrees or more.

In some embodiments, said front-pointing viewing element comprises a lens assembly providing a focal length of approximately 3-100 millimeters.

In some embodiments, said side-pointing viewing element comprises a lens assembly providing a focal length of approximately 2-33 millimeters.

In some embodiments, said tip section further comprises an opposite side-pointing viewing element pointing at a direction essentially opposite to said side-pointing viewing element.

In some embodiments, said tip section further comprises a perpendicular side-pointing viewing element pointing at a direction essentially perpendicular to said side-pointing viewing element.

In some embodiments, said endoscope is a colonoscope.

In some embodiments, fields of view of said front-pointing viewing element and side-pointing viewing element are at least partially overlapping, such that an object of interest viewed via said side-pointing viewing element remains in the field of view of said side-pointing viewing element while said tip section is being turned towards the object, and at least until the object becomes visible through said front-pointing viewing element.

In some embodiments, said utility cable comprises: a fluid channel for providing a fluid to at least one of said injectors, a data cable for receiving video signals from said front and side-pointing cameras, a power cable for providing electrical power to said front and side-pointing cameras and to said discrete front and side illuminators, an optic fiber or any combination thereof. According to alternative embodiments, any channel, fiber and/or cable can be driven independently.

In some embodiments, said controller is configured to process and combine video signals received from the cameras (for example, front and side-pointing cameras) into a single panoramic video view.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. It is intended that the embodiments and figures disclosed herein are to be considered illustrative rather than restrictive. The figures are listed below.

DETAILED DESCRIPTION

An aspect of some embodiments relates to an endoscope having a tip section equipped with two or more viewing elements. According to one embodiment, one of the viewing elements is positioned at a distal end of the tip section and points forward, and the remaining viewing element(s) is positioned further back in the tip section, and points sideways.

According to another embodiment, one of the viewing elements is positioned at a distal (front) end surface of the tip section and points forward, and the remaining viewing element(s) is positioned further back in the tip section, and points sideways.

This configuration, advantageously, may allow for a higher rate of detection, compared to conventional configurations, of pathological objects that exist in the body cavity in which the endoscope operates.

The cameras and optionally other elements that exist in the tip section (such as a light source, a working channel, a fluid injector and/or the like) are uniquely scaled, configured and packaged so that they fit within the minimalistic space available inside the tip section, while still providing valuable results.

Figure 1:
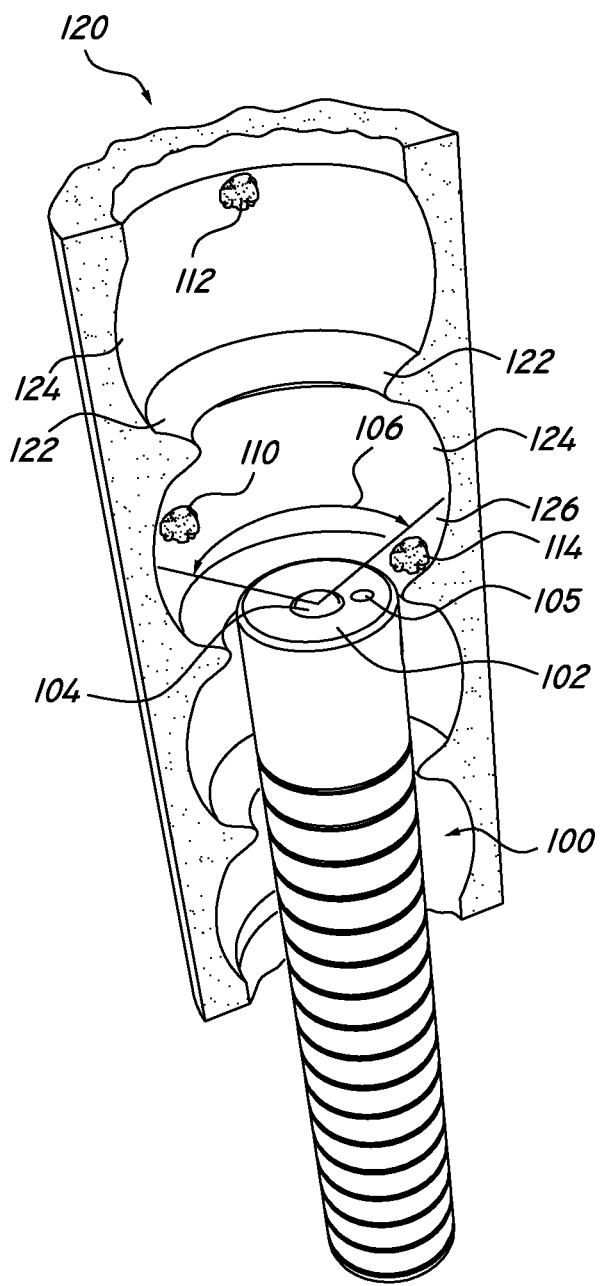
FIG. 1 shows a cross sectional view of a prior art endoscope.

Reference is now made to FIG. 1, which shows a cross sectional view of a prior art endoscope, in this example a colonoscope 100, used within a colon 120 of a patient. The human colon includes a series of annular muscles which appear in this figure as folds 122 protruding from an inner surface 124 of the colon.

Endoscope 100 includes a front-pointing camera 104 positioned at a distal end 102 of the colonoscope. Camera 104 typically has a wide field of view 106. When endoscope 100 is used within a body cavity such as colon 120, the operator advances the endoscope 100 while viewing images (commonly a video feed) transmitted by camera 104. When a polyp, such as polyp 110 or 112 is discovered on a wall of colon 120, the operator may insert a surgical tool (not shown) through a working channel 105 to remove, treat and/or extract a sample of the polyp or its entirety for biopsy.

However, in some cases, a polyp, such as polyp 114 may be located on an inner side of a fold 126, such that it is hidden from the field of view 106 of camera 104. This phenomena is said to greatly contribute to the common statistics, according to which as many as 12-24% of polyps are missed during colonoscopy. Missing polyps, or a "false negative" diagnosis, may result in late discovery of cancer.

Figure 2:
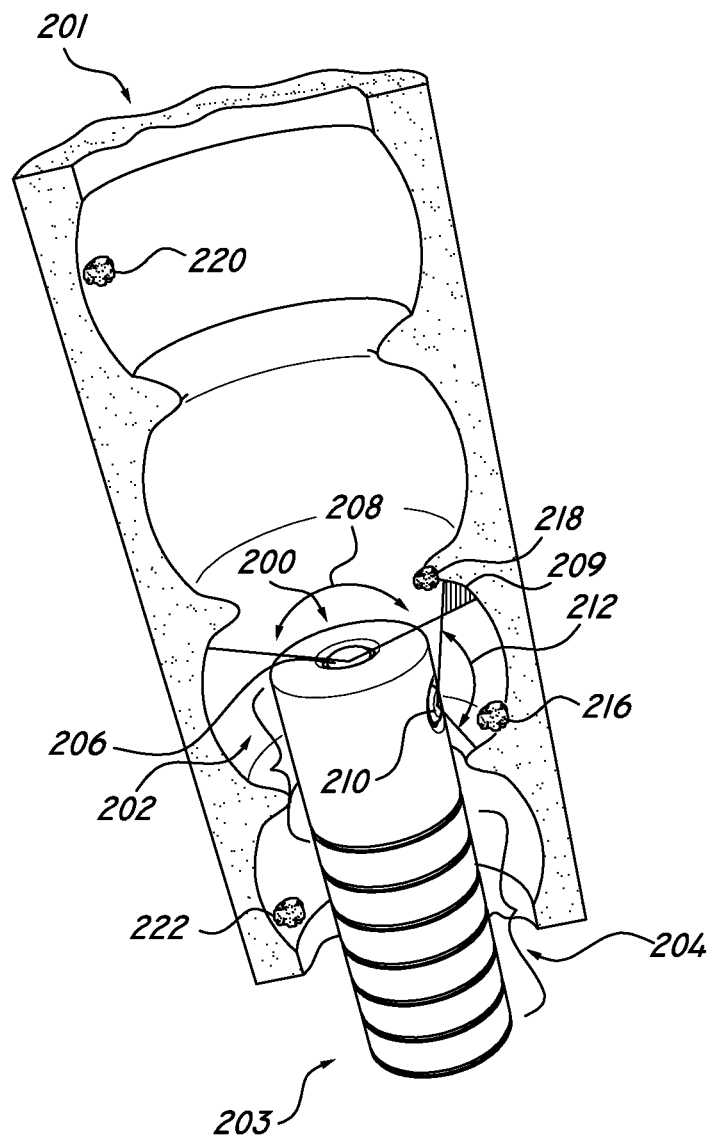
FIG. 2 shows a cross section of a multi-camera endoscope, according to some embodiments.

Reference is now made to FIG. 2, which shows a cross section of a multi-camera endoscope 200, according to an embodiment. Endoscope 200 may include an elongated shaft 203 (not fully shown) terminating with a tip section 202 which is turnable by way of a bending section 204. Advantageously, tip section may include a front-pointing camera 206 as well as a side-pointing camera 210. While front-pointing camera 206 may be able to detect, based on its field of view 208, polyps such as polyps 218 and 220, side-pointing camera 210 may be further able to detect polyps which are normally hidden from the front-pointing camera, such as polyp 216. By rotating endoscope 200 around its longitude, side-pointing camera 210 may detect polyps circumferentially, 360 degrees around the endoscope. This may enable the detection of polyps such as a polyp 222, which is, similar to polyp 216, located on an inner side of a fold. In other configurations (not shown), two or more side-pointing cameras may exist in the tip section, each having a different (or an overlapping, to some degree) field of view.

Advantageously, the fields of view of front-pointing camera 206 and side-pointing camera 210 are at least partially overlapping, such that an object of interest (such as a polyp or another pathology) viewed via the side-pointing camera remains in the field of view of this camera while the tip section is being turned towards the object, and at least until the object becomes visible through the front-pointing camera. This may be beneficial when a polyp is discovered by side-pointing camera 210, and the operator desires to perform a surgical operation on that polyp using a surgical tool inserted through a working channel (not shown in the figure) which has an opening in a distal end surface of tip section 202, next to front-pointing camera 206. For performing the surgical operation, tip section 202 may need to be turned towards the polyp. It may greatly assist the operator if the fields of view of front-pointing camera 206 and side-pointing camera 210 have some overlap, so that the polyp remains in sight throughout the turning of the tip section and the operator does not get disoriented.

Figure 3:
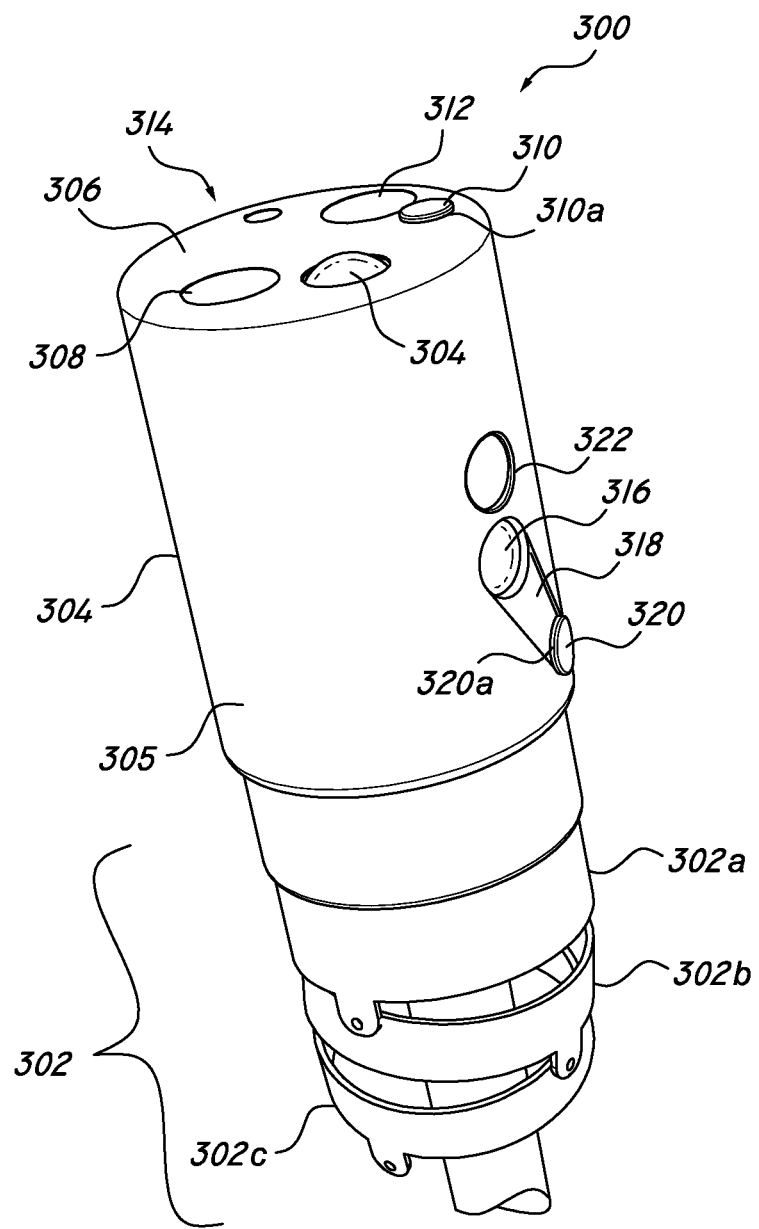
FIG. 3 shows a perspective view of a multi-camera endoscope, according to some embodiments.

Reference is now made to FIG. 3, which shows a perspective view of a multi-camera endoscope 300 in more detail, according to an embodiment. Endoscope 300 may include an elongated shaft (not shown), a bending section (partially shown) 302 and a tip section 304 which terminates the endoscope.

Bending section 302 may include a plurality of links, such as links 302a-c, which enable the turning of tip section 304 in different directions. In a different configuration (not shown), a bending section may be constructed differently, as long as it enables the turning of the tip section in different directions. Bending section 302 may be covered with an elastic sheath (not shown), which may also extend to cover the elongated shaft.

Tip section 304 may include therein a front-pointing camera 304 which may capture images through a hole in a distal end surface 306 of the tip section. A discrete front illuminator 308, which is optionally a light-emitting diode (LED), may be associated with front-pointing camera 304 and used for illuminating its field of view through another hole in distal end surface 306. The LED may be a while light LED, an infrared light LED, a near infrared light LED or an ultraviolet light LED. The term "discrete", in regard to front illuminator 308, may refer to an illumination source which generates light internally—in contrast to a non-discrete illuminator which may be, for example, a fiber optic merely transmitting light generated remotely. In a different configuration (not shown), two or more discrete front illuminators may be present in the tip section, such as for supplying overall stronger illumination and/or for increasing the angular coverage of the illumination. These two or more discrete front illuminators may be located next to one another so that they share a same protective window on the distal end surface of the tip section.

A front fluid injector 310 may be used for cleaning at least one of front-pointing camera 304 and discrete front illuminator 308. Front fluid injector 310 may be slightly elevated from distal end surface 306, to enable it to inject fluid, from its side 310a, onto front-pointing camera 304 and discrete front illuminator 308. Front fluid injector 310 may be configured to inject fluids such as water, air and/or the like.

Distal end surface 306 may further include a hole defining a working channel 312. Working channel 312 may be a hollow tube configured for insertion of a surgical tool to operate on various tissues. For example, miniature forceps may be inserted through working channel 312 in order to remove a polyp or sample of which for biopsy.

A pathway fluid injector 314, defined by another hole in distal end surface 306, may be used for inflating and/or cleaning the body cavity into which endoscope 300 is inserted. Inflation may be performed by flowing air or another gas through pathway fluid injector 314, and may be beneficial for cases in which the body cavity, such as the colon, is shriveled or otherwise does not allow for efficient inspection. Cleaning may be achieved, for example, by injecting a liquid, such as water or saline, on an unclean area of the body cavity. Furthermore, pathway fluid injector 314 (or a different tube, not shown) may be used for applying suction, in order to evacuate various liquids and/or solids which exist in the body cavity and interfere with the inspection.

Tip section 304 may further include therein a side-pointing camera 316 which may capture images through a hole in a cylindrical surface 305 of the tip section. A discrete side illuminator 322, which is optionally similar to discrete front illuminator 308, may be associated with front-pointing camera 304 and used for illuminating its field of view through another hole in cylindrical surface 305. In a different configuration (not shown), two or more discrete side illuminators may be present in the tip section, such as for supplying overall stronger illumination and/or for increasing the angular coverage of the illumination. These two or more discrete side illuminators may be located next to one another so that they share a same protective window on the cylindrical surface of the tip section.

A side fluid injector 320 may be used for cleaning at least one of side-pointing camera 304 and discrete side illuminator 322. In order to prevent tissue damage when cylindrical surface 305 of tip section 304 contacts a side wall of the body cavity, side fluid injector 320 and side-pointing camera 316 may be located in a depression 318 in the cylindrical surface. This way, side fluid injector 320 may be elevated from depression 318 but still not significantly protrude from the level of cylindrical surface 305. The elevation of side fluid injector 320 may enable it to inject fluid, from its side 320a, onto side-pointing camera 316. In an alternative configuration (not shown), one or more discrete side illuminators may also be included in the depression, so that fluid injected from the side fluid injector may reach them. In yet another configuration (not shown), a side-pointing camera, one or more side illuminators and a side fluid injector may not be located in a depression, but rather be on essentially the same level as the cylindrical surface of the tip section.

Figure 4:
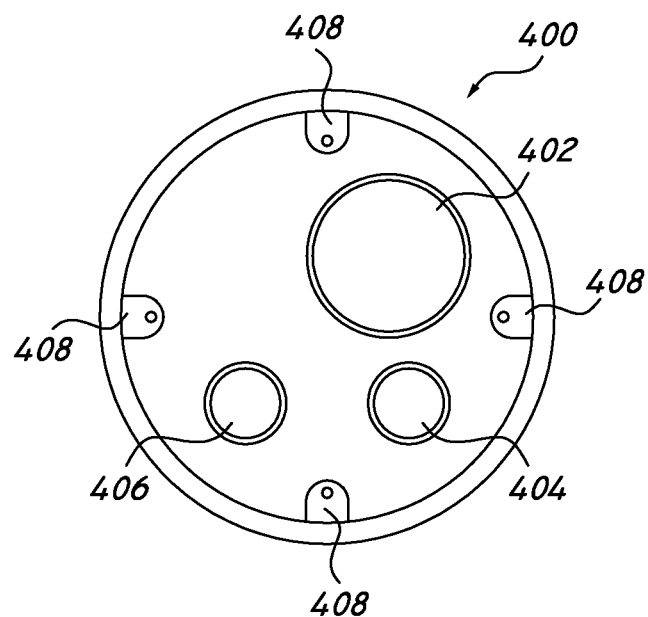
FIG. 4 shows a cross-sectional view of a bending section of a multi-camera endoscope, according to some embodiments.

Reference is now made to FIG. 4, which shows a cross-sectional view of a bending section 400 of a multi-camera endoscope, such as multi-camera endoscope 300 of FIG. 3. A plurality of steering cable eyes, such as four eyes 408, are positioned on the internal walls of bending section 400. Through these eyes 408, steering cables are threaded, to enable the maneuvering of bending section 400. Bending section 400 may also include a working channel 402, through which surgical tools may be inserted, a fluid channel 406, through which fluids and/or liquids may be infused, and an electrical channel 404, through which a plurality of electrical cables may be threaded, for transmitting video signals from the cameras and for supplying power to the cameras and the discrete illuminators.

For simplicity of presentation, FIG. 4 only shows a single working channel 402, although in a different configuration (not shown), more than one working channel may exist, to enable the insertion of multiple surgical tools simultaneously. Similarly, only one fluid channel 406 is shown, although in a different configuration (not shown) more than one fluid channel may be used, such as for separately feeding at least one of a front fluid injector, a side fluid injector and/or a pathway fluid injector, as well as for separately providing suction through the pathway fluid injector. Additionally, FIG. 4 shows only a single electrical channel 404, but in other configurations (not shown), one or more of the electrical cables threaded through the elongated shaft and/or the bending section may be separated into a plurality of tubes, for example in order to distance cables causing magnetic induction from cables which may be influenced by this phenomena.

Figure 5:
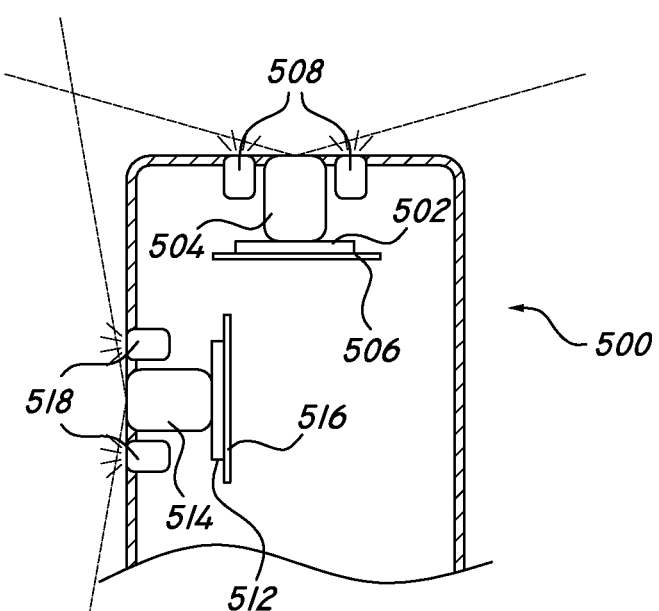
FIG. 5 shows a cross-sectional view of a tip section of a multi-camera endoscope, according to some embodiments.

Reference is now made to FIG. 5, which shows a cross-sectional view of a tip section 500 of a multi-camera endoscope, according to an embodiment. Tip section 500 may include a front-pointing image sensor 502, such as Charge Coupled Device (CCD) or a Complementary Metal Oxide Semiconductor (CMOS) image sensor. Front-pointing image sensor 502 may be mounted on an integrated circuit board 506, which may be rigid or flexible. Integrated circuit board 506 may supply front-pointing image sensor 502 with the necessary electrical power, and may derive still images and/or video feeds captured by the image sensor. Integrated circuit board 506 may be connected to a set of electrical cables (not shown) which may be threaded through an electrical channel running through the elongated shaft of the endoscope. Front-pointing image sensor 502 may have a lens assembly 504 mounted on top of it and providing the necessary optics for receiving images. Lens assembly 504 may include a plurality of lenses, static or movable, which may provide a field of view of at least 90 degrees and up to essentially 180 degrees. Lens assembly 504 may provide a focal length of about 3 to 100 millimeters. Front-pointing image sensor 502 and lens assembly 504, with or without integrated circuit board 506, may be jointly referred to as a "front pointing camera".

One or more discrete front illuminators 508 may be placed next to lens assembly 504, for illuminating its field of view. Optionally, discrete front illuminators 508 may be attached to the same integrated circuit board 506 on which front-pointing image sensor 502 is mounted (this configuration is not shown).

Tip section 500 may include a side-pointing image sensor 512, such as Charge Coupled Device (CCD) or a Complementary Metal Oxide Semiconductor (CMOS) image sensor. Front-pointing image sensor 502 may be mounted on an integrated circuit board 516, which may be rigid or flexible. Integrated circuit board 516 may supply side-pointing image sensor 512 with the necessary electrical power, and may derive still images and/or video feeds captured by the image sensor. Integrated circuit board 516 may be connected to a set of electrical cables (not shown) which may be threaded through an electrical channel running through the elongated shaft of the endoscope.

Side-pointing image sensor 512 may have a lens assembly 514 mounted on top of it and providing the necessary optics for receiving images. Lens assembly 514 may include a plurality of lenses, static or movable, which may provide a field of view of at least 90 degrees and up to essentially 180 degrees. Lens assembly 514 may provide a focal length of about 2 to 33 millimeters. Side-pointing image sensor 512 and lens assembly 514, with or without integrated circuit board 516, may be jointly referred to as a "side pointing camera".

One or more discrete side illuminators 518 may be placed next to lens assembly 514, for illuminating its field of view. Optionally, discrete front illuminators 518 may be attached to the same integrated circuit board 516 on which side-pointing image sensor 512 is mounted (this configuration is not shown).

In another configuration (not shown), integrated circuit boards 506 and 516 may be a single integrated circuit board on which both front and side-pointing image sensors 502 and 512 are mounted. For this purpose, the integrated circuit board may be essentially L-shaped.

Front and side-pointing image sensors 502 and 512 may be similar or identical in terms of, for example, field of view, resolution, light sensitivity, pixel size, focal length, focal distance and/or the like.

Optionally, side-pointing image sensor 512 and lens assembly 514 are advantageously positioned relatively close to the distal end surface of tip section 500. For example, a center of the side-pointing camera (which is the center axis of side-pointing image sensor 512 and lens assembly 514) is positioned approximately 7 to 11 millimeters from the distal end of the tip section. This is enabled by an advantageous miniaturizing of the front and side-pointing cameras, which allows for enough internal space in the tip section for angular positioning of the cameras without colliding.

Figure 6:
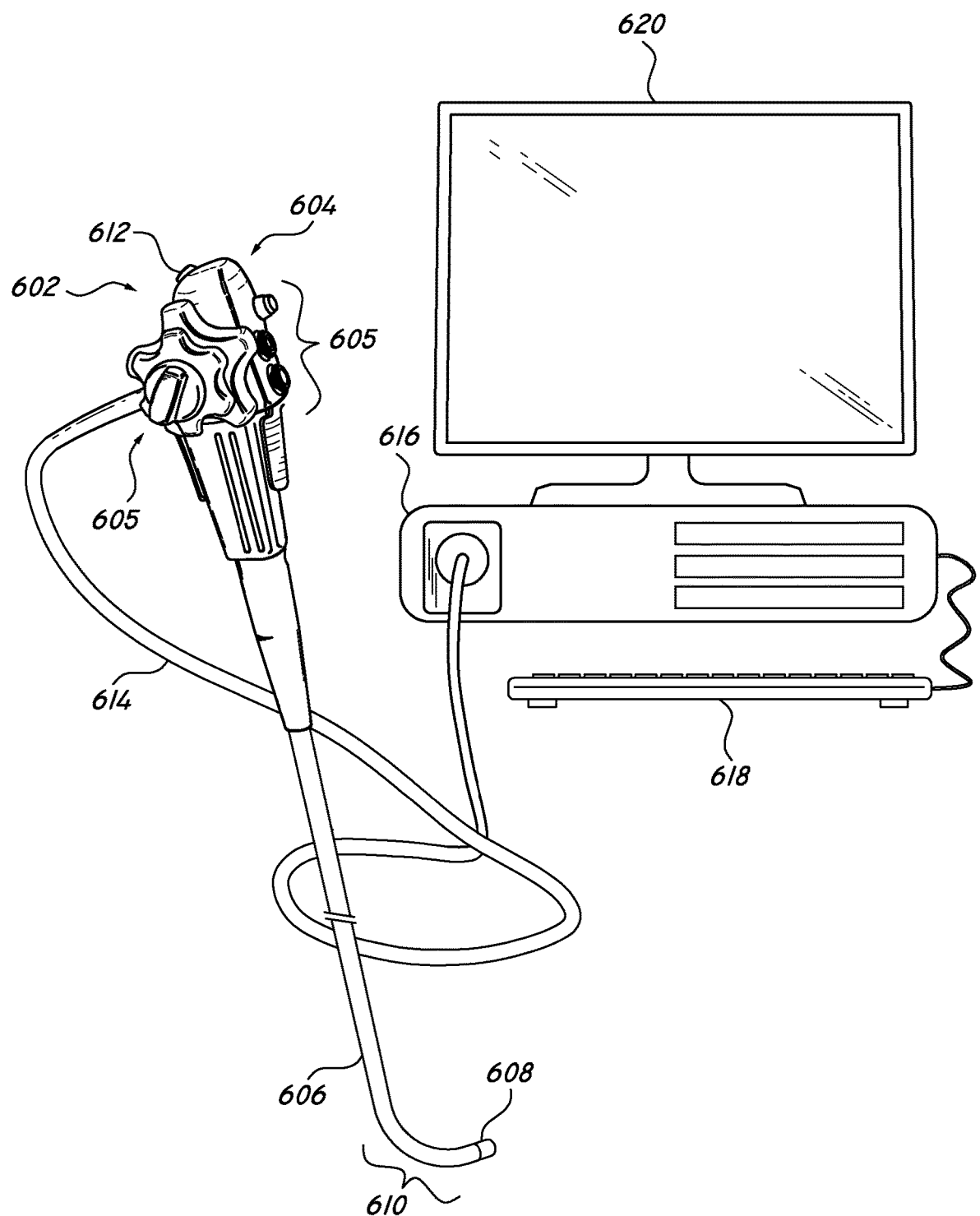
FIG. 6 shows a semi-pictorial view of a multi-camera endoscopy system, according to some embodiments.
Figure 7A:
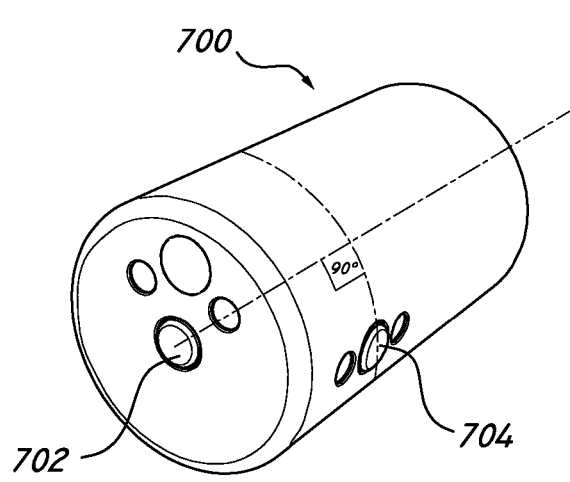
FIGS. 7A-D show perspective views of multiple tip section configurations, according to some embodiments.
Figure 7B:
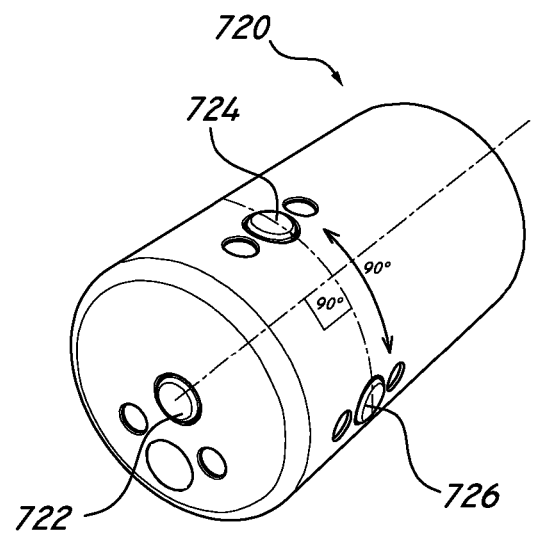
Figure 7C:
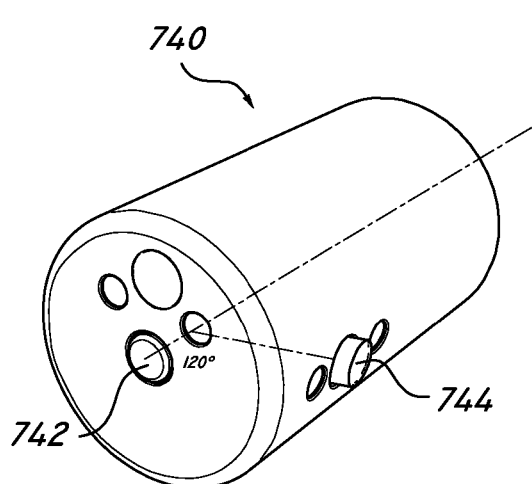
Figure 7D:
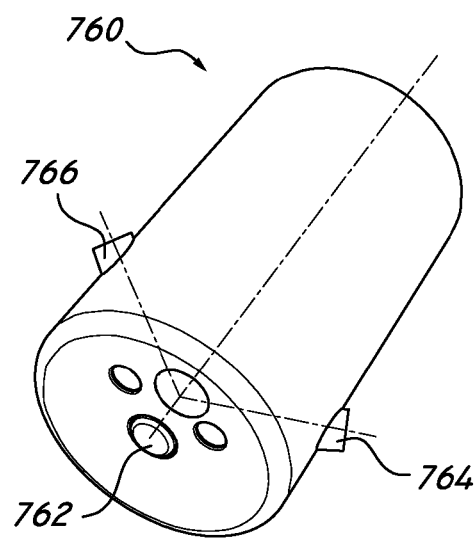

Reference is now made to FIG. 6, which shows a semi-pictorial view multi-camera endoscopy system 600. System 600 may include a multi-camera endoscope 602, such as the endoscope of FIGS. 2, 3, 4 and/or 5. Multi-camera endoscope 602 may include a handle 604, from which an elongated shaft 606 emerges. Elongated shaft 606 terminates with a tip section 608 which is turnable by way of a bending section 610. Handle 604 may be used for maneuvering elongated shaft 606 within a body cavity; the handle may include one or more knobs and/or switches 605 which control bending section 610 as well as functions such as fluid injection and suction. Handle 604 may further include a working channel opening 612 through which surgical tools may be inserted.

A utility cable 614 may connect between handle 604 and a controller 616. Utility cable 614 may include therein one or more fluid channels and one or more electrical channels. The electrical channel(s) may include at least one data cable for receiving video signals from the front and side-pointing cameras, as well as at least one power cable for providing electrical power to the cameras and to the discrete illuminators.

Controller 616 may govern power transmission to the endoscope's 602 tip section 608, such as for the tip section's cameras and illuminators. Controller 616 may further control one or more fluid, liquid and/or suction pump which supply corresponding functionalities to endoscope 602. One or more input devices, such as a keyboard 618, may be connected to controller 616 for the purpose of human interaction with the controller. In another configuration (not shown), an input device, such as a keyboard, may be integrated with the controller in a same casing.

A display 620 may be connected to controller 616, and configured to display images and/or video streams received from the cameras of multi-camera endoscope 602. Display 620 may further be operative to display a user interface for allowing a human operator to set various features of system 600.

Optionally, the video streams received from the different cameras of multi-camera endoscope 602 may be displayed separately on display 620, either side-by-side or interchangeably (namely, the operator may switch between views from the different cameras manually). Alternatively, these video streams may be processed by controller 616 to combine them into a single, panoramic video frame, based on an overlap between fields of view of the cameras.

In another configuration (not shown), two or more displays may be connected to controller 616, each for displaying a video stream from a different camera of the multi-camera endoscope.

Reference is now made to FIGS. 7A-D, in which multiple configurations 700, 720, 740 and 760 of a tip section are shown.

In configuration 700, a front-pointing camera 702 and a side-pointing camera 704 are essentially perpendicular to one another, and have, correspondingly, perpendicular fields of view.

In configuration 720, a front-pointing camera 722 is essentially perpendicular to a first side-pointing camera 724 and a second side-pointing camera 726. First and second side-pointing cameras 724-726 are pointing perpendicularly to one another, and are positioned essentially 90 degrees apart in the cylindrical surface of the tip section. In another configuration (not shown), a first and a second side-pointing cameras may be positioned more than 90 degrees apart in the cylindrical surface of the tip section, such as 120-150 degrees apart or 150-180 degrees apart. For example, the first and second side-pointing cameras may be positioned in 180 degrees apart, in opposite sides of the cylindrical surface of the tip section, so that they point in opposite directions. In yet further configurations (not shown), three or more side-pointing cameras may be positioned in the cylindrical surface of the tip section, for example, three cameras having 120 degrees in between them.

In configuration 740, a side-pointing camera 744 is pointing slightly backwards, so that it forms an angle larger than 90 degrees relative to a front-pointing camera 742. As an example, an angle of 120 degrees is shown. In another configuration (not shown), the angle is 100-145 degrees.

In configuration 760, two opposing side cameras 764 and 766 are shown, which are pointing slightly backwards, so that they each form an angle larger than 90 degrees relative to a front-pointing camera 762. As an example, an angle of 120 degrees is shown. In another configuration (not shown), the angle is 100-145 degrees.

Similarly, in other configurations (not shown), three or more side-pointing cameras may be positioned in the cylindrical surface of the tip section, each pointing slightly backwards and having an certain angle in between; in the case of three cameras, they may have an angle of 120 degrees in between them.

According to alternative embodiments, the endoscopes according to the invention, may include front/side pointing camera(s) at their tip section but may also include, in addition to or instead of one or more cameras, a fiber optic lens assembly. Such fiber optic lens assembly may include lens(es) and fiber optic(s) associated therewith, which are configured to receive light from the area of interest (tested/examined areas, such as a colon) and transfer the received light to a (video) camera which may be located in the handle of the endoscope or in the console.

Figure 8:
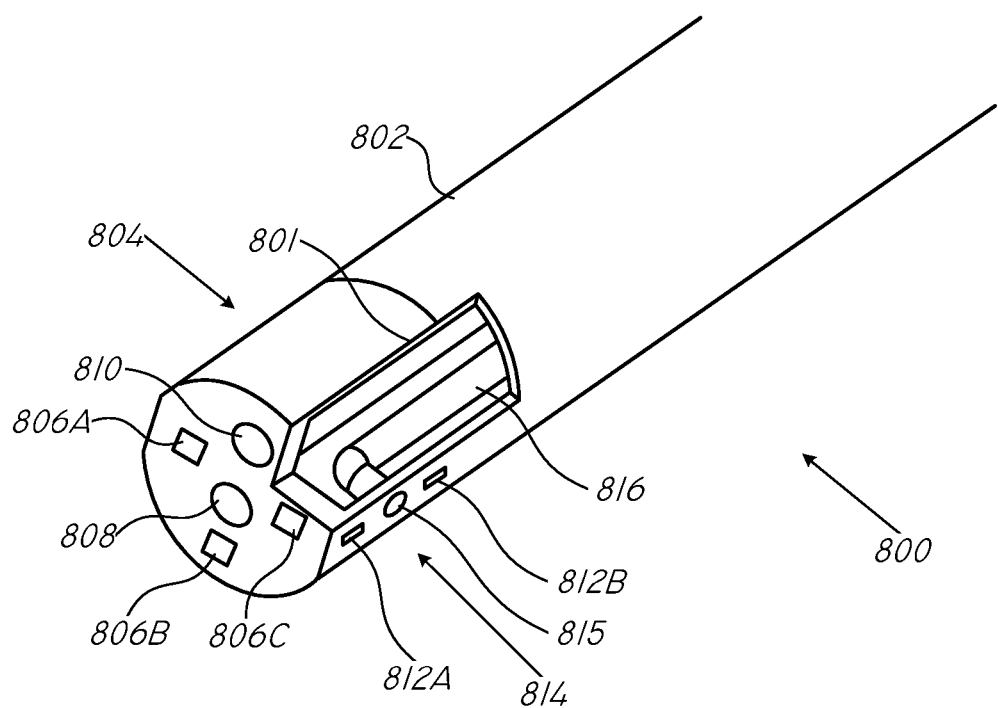
FIG. 8 shows a perspective view of a multi-viewing elements endoscope, according to some embodiments.

Reference is now made to FIG. 8, which shows, according to some embodiments, a perspective view of a multi-viewing elements endoscope, having a cut-away window to demonstrate an inner part of the endoscope, particularly the side pointing viewing element.

Endoscope 800 includes an elongated shaft 802 which typically includes a bending section (not shown) and a tip section 804 which terminates the endoscope. Endoscope 800 is illustrated with a cut-away window 801 which does not exist in real endoscopes but is presented in this figure merely to demonstrate an inner part of the endoscope, particularly the side pointing viewing element. Tip section 804 includes a front pointing viewing element 808 and three discrete illuminators (for example LEDs) 806a-c, which are associated with front-pointing viewing element 808 and are configured for illumination. Tip section 804 includes further includes one or more side pointing viewing element 814 (one is shown in this figure merely for illustrative purposes). Side pointing viewing element 814 includes lens assembly 815 and fiber optic 816. Lens assembly 815 is located at a side wall of tip section 804 and is configured to receive light from the area of interest (tested/examined areas, such as an inner part of a colon of a subject) and to transfer the received light through fiber optic 816 to a (video) camera which may be located in the handle of the endoscope or in the console.

It is noted that front-pointing viewing element 808 and side-pointing viewing element(s) 814 may be similar to each other or different. For example, front-pointing viewing element 808 may include a camera located in the tip section and side-pointing viewing element(s) 814 may include a lens assembly and a fiber optic transferring light to an image sensor located outside the tip section. According to another example, both front and side pointing viewing element may include a lens assembly and a fiber optic transferring light to an image sensor located outside the tip section. According to another example, the side-pointing viewing element(s) may include a camera located in the tip section and the front-pointing viewing element may include a lens assembly and a fiber optic transferring light to an image sensor located outside the tip section.

Tip section 804 includes further includes a working channel 810 which may be a hollow opening configured for insertion of a surgical tool to operate on various tissues. For example, miniature forceps may be inserted through working channel 810 in order to remove a polyp or sample of which for biopsy.

Tip 804 may further include other elements/components, (for example, as described herein according to various embodiments) such as additional viewing elements, fluid injector(s) for cleaning the cameras and/or there illuminators and pathway fluid injector(s) for inflating and/or cleaning the body cavity into which endoscope 800 is inserted.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

In the description and claims of the application, each of the words "comprise" "include" and "have", and forms thereof, are not necessarily limited to members in a list with which the words may be associated.

What is claimed is:

1. A medical device system comprising:
   a first side-pointing viewing element positioned at a distal tip section of the medical device system and configured to receive light from an area of interest, and an image sensor is configured to receive the light from the area of interest;
   a first illuminator configured to provide light to the area of interest;
   a first side fluid injector positioned on a first surface of the distal tip section; and
   a first depression in the first surface of the distal tip section, wherein the first illuminator and the first side fluid injector are positioned within the first depression;
   wherein the first side-pointing viewing element has a length over which an external object remains in focus in a range of 2-33 millimeters and has a center positioned 7 to 11 millimeters from a distalmost end surface of the distal tip section.

2. The system of claim 1, wherein the first side-pointing viewing element comprises a lens assembly located at the distal tip section.

3. The system of claim 1, further comprising:
   a second side-pointing viewing element positioned at the distal tip section, the second side-pointing viewing element comprising an image sensor located at the distal tip section,
   a second illuminator;
   a second side fluid injector; and
   a second depression in a second surface of the distal tip section, wherein the second illuminator and the second side fluid injector are positioned within the second depression.

4. The system of claim 1, wherein the first illuminator is a light emitting diode (LED).

5. The system of claim 1, wherein the first surface is curved.

6. The system of claim 1, wherein the first side-pointing viewing element comprises a fiber optic configured to transfer the received light to the image sensor located in a handle of the medical device system or in a console of the medical device system.

7. The system of claim 1, further comprising a second illuminator configured to illuminate at least part of a field of view of the first side-pointing viewing element.

8. The system of claim 1, wherein first side-pointing viewing element comprises a lens assembly configured to receive light from the area of interest, and the received light is transferred to the image sensor.

9. The system of claim 1, further comprising a working channel configured for insertion of a tool.

10. The system of claim 1, further comprising a front-pointing viewing element.

* * * * *